US012053292B2

(12) United States Patent
Ashdown et al.

(10) Patent No.: US 12,053,292 B2
(45) Date of Patent: Aug. 6, 2024

(54) METHOD AND SYSTEM FOR IMPROVING A PHYSIOLOGICAL RESPONSE

(71) Applicant: Lifecycle Technologies PTY LTD, Melbourne (AU)

(72) Inventors: Luke Ashdown, Melbourne (AU); Daniel Trenton, Melbourne (AU)

(73) Assignee: LIFECYCLE TECHNOLOGIES PTY LTD., Melbourne (AU)

( * ) Notice: Subject to any disclaimer, the term of this patent is extended or adjusted under 35 U.S.C. 154(b) by 603 days.

(21) Appl. No.: 15/533,365

(22) PCT Filed: Dec. 3, 2015

(86) PCT No.: PCT/AU2015/050762
§ 371 (c)(1),
(2) Date: Jun. 5, 2017

(87) PCT Pub. No.: WO2016/086271
PCT Pub. Date: Jun. 9, 2016

(65) Prior Publication Data
US 2017/0360356 A1 Dec. 21, 2017

(30) Foreign Application Priority Data
Dec. 5, 2014 (AU) .................. 2014904929

(51) Int. Cl.
*A61B 5/00* (2006.01)
*A61B 5/0205* (2006.01)
(Continued)

(52) U.S. Cl.
CPC .............. *A61B 5/41* (2013.01); *A61B 5/0022* (2013.01); *A61B 5/02055* (2013.01);
(Continued)

(58) Field of Classification Search
CPC .............. C07K 14/4705; C07K 14/475; C07K 14/521; C07K 14/7155; C07K 14/745; C07K 16/244; C07K 16/248; C07K 2317/14; C07K 14/52; C07K 14/575; C07K 14/71; C07K 14/715; G01N 33/57488; G01N 2333/47; G01N 2800/52; G01N 2800/56; G01N 33/50; G01N 33/68; G01N 2800/50; G01N 2800/60; G01N 2800/7095; G01N 2333/4737; G01N 33/57484; G01N 33/57492; G01N 35/00871; G01N 15/06; G01N 2015/008; G01N 2015/0084; G01N 2333/475; G01N 2333/70514; G01N 2333/70517; G01N 2333/70539; G01N 2333/71; G01N 33/5302; G01N 33/56972; G01N 33/6803; G01N 33/92; B01L 2300/0636; G16H 10/40; G16H 10/20; G16H 10/60; G16H 20/10; G16H 20/17; G16H 20/60; G16H 50/20; G16H 50/50; G16H 50/70; G16H 50/80; G16H 70/60; G16H 70/20; G16H 40/20; G16H 40/67; G16H 50/30; G16H 20/30; G16H 40/63; G16H 20/40; G16H 40/60; G16H 15/00; G16H 40/40; G16H 80/00; A61B 5/0833; A61B 5/14507; A61B 5/14546; A61B 5/6833; A61B 5/145; A61B 2017/3492; A61B 5/0004; A61B 5/0022; A61B 5/05; A61B 5/72; A61B 5/742; A61B 2562/04; A61B 5/01; A61B 5/0205; A61B 5/1455; A61B 5/14551; A61B 5/165; A61B 5/412; A61B 5/42; A61B 5/4806; A61B 5/7203; A61B 5/7221; A61B 5/7246; A61B 5/7264; A61B 5/746; A61B 5/00; A61B 5/0006;
(Continued)

(56) References Cited

U.S. PATENT DOCUMENTS 8,234,129 B2 * 7/2012 Michon .................. G16B 20/00
600/300
8,540,644 B2 * 9/2013 Husheer ............... A61B 5/0031
600/549
(Continued)

FOREIGN PATENT DOCUMENTS

CN 101529228 A 9/2009
JP 2008-512654 A 4/2008
(Continued)

OTHER PUBLICATIONS

Gokhale et al. Cytokine response to strenuous exercise in athletes and non-athletes—an adaptive response. Cytokine (2007) vol. 40 p. 123-127. (Year: 2007).*

(Continued)

Primary Examiner — Mary K Zeman
(74) Attorney, Agent, or Firm — Gary J. Gershik

(57) ABSTRACT

A system and method for determining the immune status or immune cycle in a subject is provided. A sampling component for obtaining physiological data from the subject is provided together with a data storage component for storing the physiological data obtained from the subject. A processing component is provided to analyse the physiological data and thereby determine the immune status or periodicity of the immune cycle and the immune cycle of the subject. An output component for outputting the immune status or periodicity of the immune cycle, and the immune cycle of the subject and/or the future status or immune cycle of the subject is provided.

15 Claims, 18 Drawing Sheets

(51) Int. Cl.
| | |
|---|---|
| A61B 10/00 | (2006.01) |
| A63B 24/00 | (2006.01) |
| A63B 71/06 | (2006.01) |
| G01N 33/48 | (2006.01) |
| G01N 33/50 | (2006.01) |
| G06F 7/06 | (2006.01) |
| G09B 5/06 | (2006.01) |
| G09B 19/00 | (2006.01) |
| G16H 10/60 | (2018.01) |
| G16H 20/30 | (2018.01) |
| G16H 20/40 | (2018.01) |
| G16H 20/60 | (2018.01) |
| G16H 40/67 | (2018.01) |
| G16H 50/20 | (2018.01) |
| G16H 70/60 | (2018.01) |
| A61B 5/021 | (2006.01) |
| A61B 5/024 | (2006.01) |
| A61B 5/145 | (2006.01) |

(52) U.S. Cl.
CPC ............ *A61B 5/4857* (2013.01); *A61B 5/486* (2013.01); *A61B 5/7275* (2013.01); *A61B 10/0051* (2013.01); *A63B 24/0075* (2013.01); *A63B 71/0622* (2013.01); *G01N 33/48* (2013.01); *G01N 33/50* (2013.01); *G06F 7/06* (2013.01); *G09B 5/06* (2013.01); *G09B 19/0092* (2013.01); *G16H 20/30* (2018.01); *G16H 20/40* (2018.01); *G16H 50/20* (2018.01); *G16H 70/60* (2018.01); *A61B 5/021* (2013.01); *A61B 5/02405* (2013.01); *A61B 5/145* (2013.01); *A63B 2071/0625* (2013.01); *G01N 2800/24* (2013.01); *G01N 2800/56* (2013.01); *G16H 10/60* (2018.01); *G16H 20/60* (2018.01); *G16H 40/67* (2018.01)

(58) Field of Classification Search
CPC ... A61B 5/0008; A61B 5/0024; A61B 5/0071; A61B 5/02055; A61B 5/02416; A61B 5/1118; A61B 5/14539; A61B 5/14542; A61B 5/6802; A61B 5/681; A61B 5/6813; A61B 5/7235; A61B 5/7257; A61B 5/7267; A61B 5/7275; A61B 5/7282; A61B 5/74; A61B 5/743; A61H 2201/165; A61H 2201/5043; C40B 30/04; C40B 50/06; G06N 20/00; G06N 5/04; G06N 3/0427; G06N 3/08; G06N 3/088; G06N 7/005; G06N 3/0472; G06N 5/003; G06N 5/02; G06N 5/045; G16B 20/00; G16B 25/10; G16B 40/00; G16B 40/10; G16B 40/20; G16B 5/00; G16B 5/20; G16B 20/20; G16B 30/00; G16B 15/00; G16B 15/20; G16B 20/10; G16B 25/00; G16B 30/10; G16B 40/30; G16B 35/00; G16B 99/00; A61K 39/00; A61P 31/00; A61P 37/00; C12N 7/00; C12N 1/00; C12Q 1/6883; C12Q 2600/158

See application file for complete search history.

(56) References Cited

U.S. PATENT DOCUMENTS

| | | | | |
|---|---|---|---|---|
| 9,460,263 | B2* | 10/2016 | Holmes | G16H 50/70 |
| 9,558,318 | B2* | 1/2017 | Hoeng | G16B 5/00 |
| 9,974,018 | B2* | 5/2018 | San Vicente | H04W 52/0209 |
| 10,073,952 | B2* | 9/2018 | Apte | G16H 50/20 |
| 10,086,232 | B2* | 10/2018 | Hoffman | G06F 3/165 |
| 10,120,413 | B2* | 11/2018 | Aimone | A61B 5/486 |
| 10,278,624 | B2* | 5/2019 | Short | G06F 16/285 |
| 10,339,464 | B2* | 7/2019 | Martin | G16H 50/20 |
| 10,368,741 | B2* | 8/2019 | Courtemanche | A61B 5/0205 |
| 2007/0202119 | A1 | 8/2007 | Ashdown | |
| 2008/0091471 | A1 | 4/2008 | Michon et al. | |
| 2008/0261258 | A1* | 10/2008 | Smith | G01N 33/6842 |
| | | | | 435/29 |
| 2010/0285082 | A1* | 11/2010 | Fernandez | C12Q 1/68 |
| | | | | 424/422 |
| 2011/0137851 | A1* | 6/2011 | Cavet | A61P 19/02 |
| | | | | 706/54 |
| 2012/0303284 | A1* | 11/2012 | Leontovich | G16H 20/10 |
| | | | | 702/19 |
| 2013/0080381 | A1* | 3/2013 | Stergiou | G06F 19/00 |
| | | | | 706/59 |
| 2013/0151165 | A1* | 6/2013 | Ashdown | A61P 35/00 |
| | | | | 702/19 |
| 2013/0218475 | A1 | 8/2013 | Ashdown et al. | |
| 2014/0310019 | A1* | 10/2014 | Blander | G06Q 10/10 |
| | | | | 705/2 |
| 2014/0344208 | A1* | 11/2014 | Ghasemzadeh | G06F 19/00 |
| | | | | 706/52 |
| 2015/0200838 | A1* | 7/2015 | Nadeau | H04B 10/27 |
| | | | | 398/58 |
| 2015/0379400 | A1* | 12/2015 | Tatourian | H04L 67/22 |
| | | | | 706/46 |
| 2018/0144820 | A1* | 5/2018 | Grimmer | G06F 16/9535 |
| 2018/0308585 | A1* | 10/2018 | Holmes | G16H 50/70 |
| 2018/0357359 | A1* | 12/2018 | Markovic | G16B 40/00 |

FOREIGN PATENT DOCUMENTS

| | | | |
|---|---|---|---|
| JP | 2011-511297 A | 4/2011 | |
| KR | 10-2009-0003748 A | 1/2009 | |
| RU | 2371727 C2 | 10/2009 | |
| WO | WO-2009/061514 A1 | 5/2009 | |
| WO | WO-2010135781 A1 * | 12/2010 | ............... A61B 5/41 |

OTHER PUBLICATIONS

Helwatkar et al. Sensor technology for animal health monitoring. Proceedings for the 8th International conference on sensing technology, Sep. 2-4, Liverpool, UK 2013 (Year: 2013).*
Lim et al. Human thermoregulation and measurement of body temperature in exercise and clinical settings. Ann Acad Med Singapore (2008) vol. 37:347-353. (Year: 2008).*
McGrath et al. Wellness, fitness and lifestyle sensing applications. In: sensor technologies. (2013) Apress, Berkley, CA. Chapter 10. (Year: 2013).*
Petersen, A.M. et al. The anti-inflammatory effect of exercise. J Appl Physiol. (2005) vol. 98: 1154-1162. (Year: 2005).*
Wikipedia, Immunoglobulin D, downloaded Jun. 2, 2021, one page. (Year: 2021).*
Engel (2014) Hormonal, Metabolic, and Cardiorespiratory responses of Young and Adult athletes to a single session of high intensity cycle exercise. Pediatric Exercise Science, 26(4) p. 485-494. Abstract Only Provided, One Page. (Year: 2014).*
Brenner (1999) Impact of three different types of exercise on components of the inflammatory response. Eur J Appl Physiol 80:452-460. (Year: 1999).*
Davidson (2020) Vital sign circadian rhythms in patients prior to discharge from an ICU: a retrospective observational analysis of routinely recorded physiological data. Critical Care 24:181. 13 pages. (Year: 2020).*
Cell Signalling Technology Immune Cell Markers, downloaded from website 2022 (Year: 2022).*
Biomarker definition from NCI Dictionaries downloaded 2022. (Year: 2022).*
Thackar (2010) dynamic models of immune responses: what is the ideal level of detail? Theoretical biology and medical modeling vol. 7: 35, 7 pages. (Year: 2010).*
Zhang, Y. et al. (Dec. 2013) Principal trend analysis for time course data with applications in genomic medicine. The Annals of Applied Statistics vol. 7 No. 4, p. 2205-2228. (Year: 2013).*

(56) References Cited

OTHER PUBLICATIONS

Chen, Y-C et al. (Jan. 2014) Non-parametric and adaptive modelling of dynamic periodicity and trend with heteroscedastic and dependent errors. Journal of the Royal Statistical Society; Statistical methodology series B, vol. 76 No. 3, 651-682. (Year: 2014).*
Austin-Ketch, T.[abbreviated AK], (Jun. 2008) Buffalo Cardio-Metabolic Occupational Police Stress Study: An Exploratory Analysis of Post-traumatic Stress, Depression, Metabolic Syndrome and Salivary Cortisol. Dissertation, State University of New York at Buffalo. 342 pages. (Year: 2008).*
Nguyen, T. T. et al. (Jan. 2013) An agent-based model of cellular dynamics and circadian variability in human endotoxemia. PLOS ONE 8:1 e55550, 14 pages. (Year: 2013).*
Maslove, D.M. et al. (Apr. 2014) Gene expression profiling in sepsis: timing tissue and translational considerations. Trends in Molecular Medicine 20:4 p. 1-10. (Year: 2014).*
Alizon, S. (2008) Multiple infections, immune dynamics and the evolution of virulence. The American naturalist 172:4 p. E161-E168. (Year: 2008).*
Grassly, N. C. et al. (2006) seasonal infectious disease epidemiology. Proceedings of the royal society B, 273: 2541-2550. (Year: 2006).*
Kidd, S.A. (2010) Sleep and Cortisol in preschool aged children with autism and typically developing children. UC Berkley, 244 pages. (Year: 2010).*
BioRad 2022 Lineage biomarkers of the human immune system. Downloaded from the web Oct. 27, 2022 (Year: 2022).*
Nilsson (2022) Doing well-being: self reported activities are related to subjective well being. PLOS ONE vol. 17, No. 6 e0270503, 23 pages. (Year: 2022).*
WHO: Global recommendations on physical activity for health (2010) downloaded Oct. 27, 2022. 60 pages. (Year: 2022).*
Farhud (2015) Impact of Lifestyle on Health. Iran J Public Health, vol. 44, No. 11, p. 1442-1444. (Year: 2015).*
Iwai et al. (2000) leisure-time physical activity and related lifestyle characteristics among middle aged Japanese. Journal of Epidemiology vol. 10, No. 4, 2000. p. 226-233. (Year: 2000).*
On biostatistics and clinical trials: (2016) Surrogate biomarkers, diagnostic biomarkers, prognostic biomarkers and predictive biomarkers. 3 pages. (Year: 2016).*
Dupre et al. (2018) Inflammation and cancer: what a surgical oncologist should know. European Journal of Surgical Oncology vol. 44, p. 566-570. (Year: 2018).*
Boles, J. et al. 2003 Correlation of body temperature with protection against staphylococcal enterotoxin B exposure and use in determining dose-schedule. Vaccine, vol. 21, p. 2791-2796. (Year: 2003).*
Silver, A. C. (2012) The circadian clock controls Toll-like receptor 9-mediated innate and adaptive immunity. Immunity, vol. 36, p. 251-261. (Year: 2012).*
Petrovsky, N. et al. The chronobiology of human cytokine production. In: cytokines and cytokine receptors, published 2000, CRC press, ebook. Ch34, 15 pages. (Year: 2000).*
Pollmacher, T. et al. (1996) Diurnal variations in the human host response to endotoxin. The Journal of Infectious Disease, vol. 174, p. 1040-1045. (Year: 1996).*
Kaaijk, P. et al. (2013) Nonclinical vaccine safety evaluation: advantages of continuous temperature monitoring using abdominally implanted data loggers. J Applied Toxicology, vol. 33, p. 521-526. (Year: 2013).*
Stern et al. (2009) Long-range correlations in rectal temperature fluctuations of healthy infants during maturation. PLOS One, vol. 4, issue 7, e6431, 9 pages. (Year: 2009).*
Stenfeldt (2011) analysis of the acute phase responses of SAA, haptoglobin and interferon type 1 in cattle experimentally infected with foot and mouth disease serotype O. Veterinary research, vol. 42, e66, 10 pages. (Year: 2011).*
Jain, S. et al. (2011) Acute-phase proteins: as a diagnostic tool. Journal of Pharmacy and Bioallied Sciences, vol. 3, issue 1, p. 118-127. (Year: 2011).*
Forster, R. (2012) study designs for the nonclinical safety testing of new vaccine products. Journal of Pharmacological and toxicological methods, vol. 66, p. 1-7. (Year: 2012).*
Examination Report No. 1 issued in Australia Patent Application No. 2015358294 dated Jun. 12, 2020 (Jun. 12, 2020). 9 pages.
Johnson, Lucy. "Cancer 'code' is cracked." Daily Express, Mar. 7, 2010, https://www.express.co.uk/news/uk/162047/Cancer-code-is-cracked. 5 pages.
Second Official Action issued in China Patent Application No. 201580066824 dated May 18, 2020 (May 18, 2020). 12 pages. [Chinese Language].
International Search Report Issued in PCT/AU2015/050762 on Apr. 8, 2016.
First substantive Examination Report issued in Israeli Patent Application No. 252690, dated Jul. 12, 2020 (Jul. 12, 2020). 4 pages. [Includes English Language Translation].
First Official Action issued in China Patent Application No. 201580066824.1 dated Aug. 27, 2019 (Aug. 27, 2019). 15 pages. [Chinese Language].
Yan et al. (2013) "Experimental study on non-injury diagnosis of pre-competition training of young swimmers." Journal of Shandong Institute of Physical Education and Sports, 29(1):91-95.
Notice of Reasons for Rejection issued in Japan Patent Application No. 2017-548501, mail date Sep. 30, 2019 (Sep. 30, 2019). 3 pages. [Japanese Language].
Notice of Reasons for Rejection issued in Japan Patent Application No. 2017-548501, mail date Sep. 30, 2019 (Sep. 30, 2019). 4 pages. [English Language Translation].
Official Action issued in Russia Federation Patent Application No. 2017123538/14(040850) dated May 31, 2019 (May 31, 2019). 7 pages. [English Language Translation].
Official Action issued in Russia Federation Patent Application No. 2017123538/14(040850) dated May 31, 2019 (May 31, 2019). 8 pages. [Russian Language].
Search Report issued in Russia Federation Patent Application No. 2017123538/14(040850) dated May 29, 2019 (May 29, 2019). 2 pages. [English Language Translation].
Search Report issued in Russia Federation Patent Application No. 2017123538/14(040850) dated May 29, 2019 (May 29, 2019). 2 pages. [Russian Language].
Decision of Rejection issued in Japan Patent Application No. 2017-548501, mail date Aug. 17, 2020 (Aug. 17, 2020). 3 pages. [English Language Translation].
Decision of Rejection issued in Japan Patent Application No. 2017-548501, mail date Aug. 17, 2020 (Aug. 17, 2020). 3 pages. [Japanese Language].
Search Report issued in Brazil Patent Application No. BR112017011557, dated Aug. 13, 2020. 4 pages. [Portuguese Language].
Written Opinion issued in Brazil Patent Application No. BR112017011557, dated Aug. 13, 2020. 2 pages. [English Language Translation].
Examination Report No. 1 issued in India Patent Application No. 201747019111 dated Oct. 26, 2020 (Oct. 26, 2020). 8 pages. [includes English translation].
Office Action issued in China Patent Application No. 201580066824.1 dated Dec. 1, 2020 (Dec. 1, 2020). 10 pages. [Chinese Language].
Dias, R. et al. "Immune parameters, symptoms of upper respiratory tract infections, and training-load indicators in volleyball athletes," International Journal of General Medicine, (2011), vol. 4: 837-44.
Dressendorfer, R. et al. "Performance Enhancement With Maintenance of Resting Immune Status After Intensified Cycle Training." Clinical Journal of Sport Medicine, (2002), vol. 12, pp. 301-307.
Examination Report No. 2 issued in Australia Patent Application No. 2015358294, dated May 4, 2021 (May 4, 2021). 14 pages.
Appeal Decision Cover Letter in re: Japan Patent Application No. 2017-548501 from Japanese counsel, e-mail date Nov. 9, 2021. 2 pages. [English language].
Appeal Decision issued in Japan Patent Application No. 2017-548501, mail date Oct. 18, 2021 (Oct. 18, 2021). 14 pages. [Japanese Language].
Appeal Decision issued in Japan Patent Application No. 2017-548501, mail date Oct. 18, 2021 (Oct. 18, 2021). 9 pages. [English Language Translation].

(56) References Cited

OTHER PUBLICATIONS

Examination Report issued in Canada Patent Application No. 2,969,133 dated Nov. 17, 2021 (Nov. 17, 2021). 5 pages.
Examination Report 1 issued in Mexico Patent Application No. MX/A/2017/007142, date of report Sep. 22, 2021 (Sep. 22, 2021). 5 pages. [Spanish language].
Patent Examination Report 1 issued in New Zealand Patent Application No. 732891, date of report Sep. 7, 2021 (Sep. 7, 2021). 5 pages.
Official Action issued in Korea Patent Application No. 10-2017-7018508 transmitted May 2, 2022 (May 2, 2022). 13 pages. [English Language Translation].
Patent Examination Report 3 issued in New Zealand Patent Application No. 732891, date of report May 17, 2022 (May 17, 2022). 8 pages.
Examination Report 2 issued in Mexico Patent Application No. MX/A/2017/007142, date of report Feb. 10, 2022 (Feb. 10, 2022). 10 pages. [Spanish Language Only].
Notice of Reasons for Rejection issued in Japan Patent Application No. 2020-209161, mail date Jan. 17, 2022 (Jan. 17, 2022). 3 pages. [Japanese Language].
Notice of Reasons for Rejection issued in Japan Patent Application No. 2020-209161, mail date Jan. 17, 2022 (Jan. 17, 2022). 4 pages. [English Language Translation].
Patent Examination Report 2 issued in New Zealand Patent Application No. 732891, date of report Feb. 17, 2022 (Feb. 17, 2022). 10 pages.
Oct. 10, 2022 Reexamination Report issued in connection with counterpart Chinese Patent Application No. 201580066824.1, including English language translation thereof.
Medical Exercise Physiology, edited by Wang Yang et al., China Medical Science and Technology Press, Oct. 2010, pp. 140-141(1), including English language translation of relevant pages.

* cited by examiner

EXHIBIT B

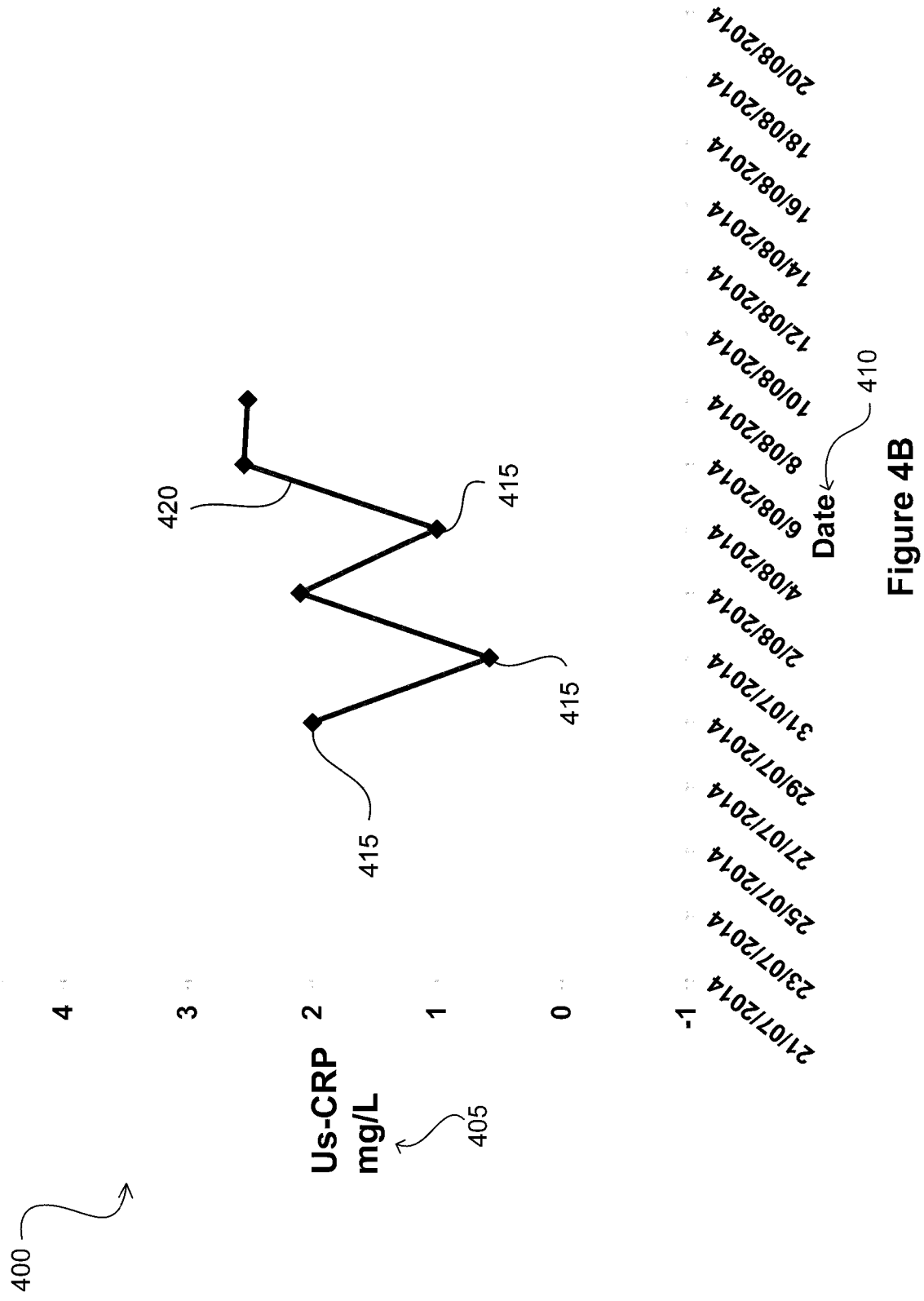

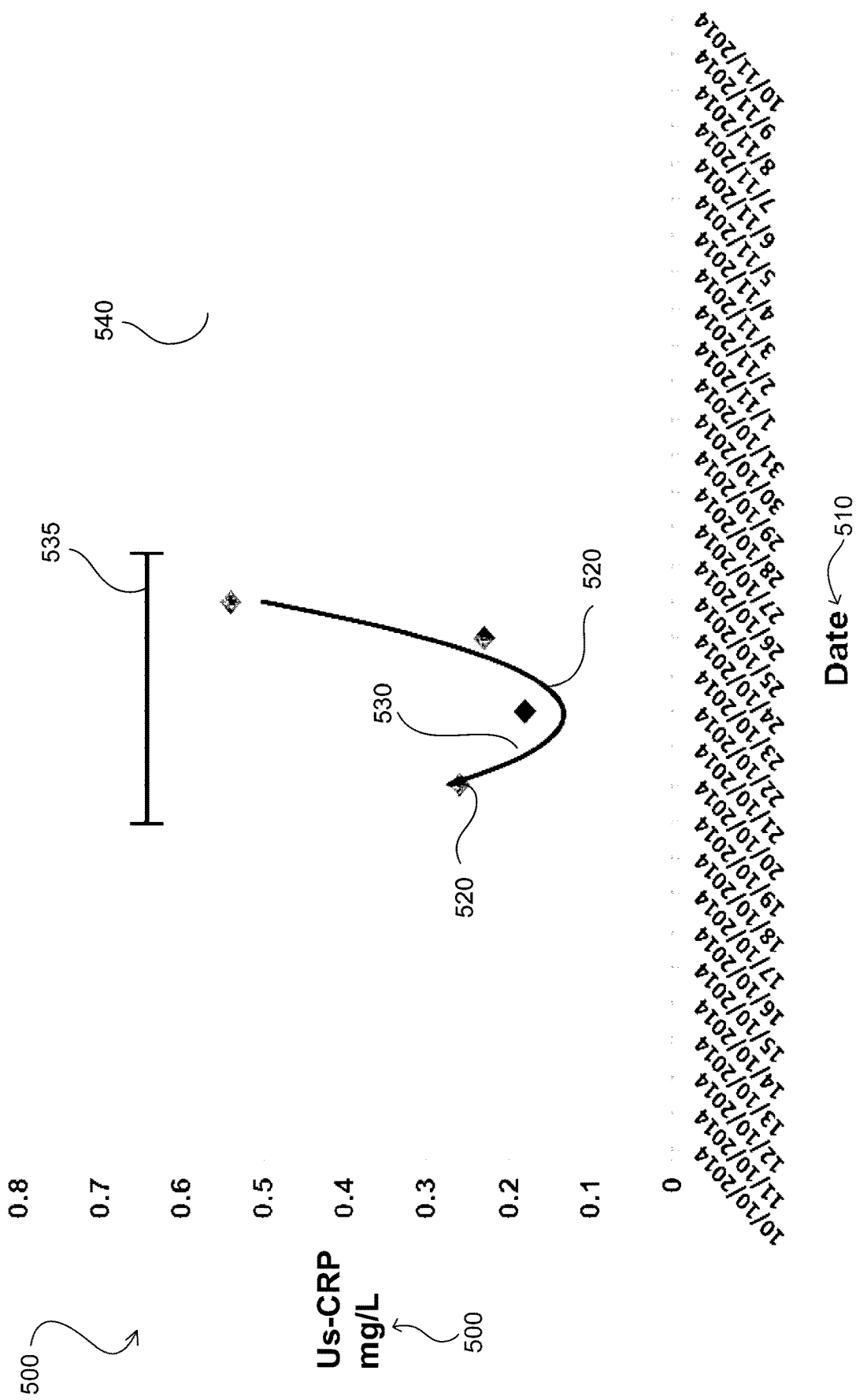

METHOD AND SYSTEM FOR IMPROVING A PHYSIOLOGICAL RESPONSE

CROSS-REFERENCES TO RELATED APPLICATIONS

This application is a national stage entry, filed under 35 U.S.C. § 371, of International Application No. PCT/AU2015/050762, filed on Dec. 3, 2015, and claims the benefit of and priority to Australian Patent Application No. 2014904929, filed Dec. 5, 2014, the entire contents of each are hereby incorporated herein by reference in their entireties and for all purposes.

TECHNICAL FIELD

The present invention relates to systems and methods for physiological and other data recording and monitoring.

BACKGROUND OF INVENTION

Individuals engage in regular and periodic (training) regimens involving physical activity, particularly individuals training to improve health, physical fitness, participate in a sports event(s) or in rehabilitation of a sports or exercise related injury. Much of this training involves physical workout periods followed by rest periods. Successful training results in improved performance. Training also involves a consideration of other aspects such as nutrition (including compositions pre and post training) which can assist with an individual's adaptation to physical loading and recovery. In addition, fixed factors such as the genetic makeup as well as other variable factors such as recent injuries or physical insults, infections and environmental factors may also play a part in successful training. Other regimens may involve the intake of dietary supplements such as calcium tablets and omega-3 capsules, or other supplements such as glucosamine, chondroitin, creatine, etc to assist with physical training and general well-being.

Individuals also engage in other regular and irregular or once-off activities to enhance their health or wellness or as preventative measures to guard against illness or disease. Examples include actions such as vaccinations against disease, vaccination against allergies, elective surgery such as plastic and or cosmetic surgery, non-urgent medical interventions such as hip and joint replacement, hormone replacement therapies, dental interventions and drug rehabilitation. Regular or irregular or once-off activities may also involve the intake of dietary supplements and/or other supplements or medications such as pain relievers or anti-inflammatory medications.

Presently, an individual's action or action plan is largely based on observation and or subjective responses based on how the individual is feeling and responses to questions about their health. Further, actions may presently be planned to coincide with externally controlled factors such as availability of trainers or doctors, business hours and or operating hours of clinics or training facilities. Further, actions may be planned around other personal commitments.

Further, the intensity of training may also be dictated by the time to prepare for an event, and the starting physical status of the individual.

It is well known to those skilled in the relevant arts that many of the activities described have been studied with respect to their impacts following the activities on the individual's immune response. There has been very little investigation with respect to the individual's immune status prior to the activities undertaken. Further, it has only been recently described that in chronic disease states the immune system of the individual exhibits a cyclical behaviour. There is a need to understand more about an individual's immune status or immune cycle so that such information can be used to provide predictive analytics and recommendations for the management of activities tailored to the individual.

The discussion of the background to the invention herein including reference to documents, acts, materials, devices, articles and the like is intended to explain the context of the present invention. This is not to be taken as an admission or a suggestion that any of the material referred to was published, known or part of the common general knowledge as at the priority date of any of the claims.

SUMMARY OF INVENTION

The present invention uses knowledge of an individual's immune status or immune cycle obtained by analysing serial measurements of biomarkers to provide predictive analytics and recommendations for the management of activities tailored to the individual.

The immune response is known to be important in maintaining health such as fighting infections. It is also known to play a role in chronic disease states such as autoimmunity and cancer as well as being involved subsequent to injury and during recovery even from exercise or surgery. The immune system is a complex system involving a number of different components and processes including cellular and innate responses and processes such as inflammation. The immune response is a co-ordinated physiological process which is well known to be initiated by insult or injury and eventually terminates homeostatically over a period of approximately two weeks.

Various factors may affect an individual's immune state, response or ability to respond. For example, nutritional factors, hormonal factors, vitamin deficiencies, high stress, high cortisol levels, and sleep deprivation, genetic factors and intense physical training. It is recognised that maintaining a healthy immune state is important in maintaining a general state of well-being.

An immune response occurs after infection or injury or surgery. This includes an initial phase which includes a cascade of processes which are well known to those in the art. The activity of the immune system and immune response can be monitored via biomarkers including but not limited to C-Reactive Protein (CRP), IL-6, Serum Amyloid A (SAA), Haptoglobin, Pro-Calcitonin and Erythrocyte Sedimentation Rate (ESR). Further, activities of the immune system or the immune state can be manifested through systemic effects such as increased body temperature, heart rate variations and variations in blood pressure which can serve as surrogate markers and can be monitored via appropriate monitoring devices such as thermometers, heart rate monitors and blood pressure monitors. The initial acute phase of the immune response is followed by a homeostatic return of the markers to normal low levels. These processes are well characterised with respect to infections, vaccinations and injuries which include accidental injuries and/or injuries as a result of surgery. There is variability in the immune response to such events between individuals. Variability has been attributed to a number of factors including but not limited to an individual's genetic makeup, age, nutritional state, disease state, medication, environmental factors, physical injury or existing trauma and stress.

Surprisingly, what we have now discovered is that the immune system in well or otherwise healthy individuals (normal), that is, in the non-chronic disease state, shows a rise and fall in immune activity in a continuously repeating pattern which is here defined as the normal immune cycle. This activity has been discerned using the same immune markers albeit at lower levels than are often seen in. Surprisingly, it has only been with the advent of the new generation of reagents with increased sensitivities, such as high sensitive C-Reactive Protein and ultrasensitive C-Reactive Protein that these fluctuations can now be accurately discerned.

Surprisingly, while immune biomarkers are well recognised as useful in the field, we have also found that body temperature is a characteristic of the immune cycle in normal individuals. It is not well known or routine to serially monitor the immune system to detect the immune cycle in healthy or non-chronically diseased individuals.

The inventors have found that in healthy or non-chronically diseased individuals there is a rise in immune activity as discerned as a rise in certain biomarkers (and is here termed the pro-inflammatory phase) which is then followed by a fall in immune activity as discerned by a fall in these biomarkers (and here termed the anti-inflammatory phase). Further, it is the status or phase of the individual's immune system at the time of an immunological trigger event such as infection, injury, vaccination or surgery that may account for some of the variability in the immune response in individuals. Reported variabilities include the magnitude or degree of the response such as a high or low level response to vaccination or short or long recovery time following injury or surgery. The individual's phase or the status of their immune cycle at the time of the insult will trigger an immune response, the magnitude or degree of which may become amplified around the pro-inflammatory phase, while in comparison the response may be minimised, comparatively less or dampened around the anti-inflammatory phase. While a heightened response is desirable following a vaccination event, the opposite, that is, a low level response is more desirable in response to injury or insult resulting from physical exercise or surgery. Thereby, the optimal timing of trigger events will be dictated by the type of activity and the desired outcome. For example, a good response or desirable response to a vaccination will be a heightened immune response including increased inflammation while, in contrast, a good or desired response to physical training or surgery will be reduced response such as reduced inflammation or soreness and lessened time in recovery and resumption of normal or planned activities.

The inventors consider that the pro-inflammatory state would cause any response to an internal or external trigger, such as muscle injury or vaccination to be more heightened than the response around the anti-inflammatory state. The response may include degree of pain, soreness, fatigue and length of time to recover to normal activities and may, but necessarily, be discerned as an relative increase in magnitude of response as measured by biomarkers. The inventors believe that timing of the trigger event with respect to the individual's immune status and cycle may explain some of the variability in responses observed between individuals and in the same individual. The inventors consider that timing with respect to the immune cycle, is an important determinant of degree of responses to vaccinations and recovery times from injury as a result of physical insult.

According to a first aspect, the present invention provides a system for determining the immune status or immune cycle in a subject, the system including: a sampling component for obtaining physiological data from the subject; a data storage component for storing the physiological data obtained from the subject; a processing component to analyse the physiological data thereby determining on that basis the immune status and/or periodicity of the immune cycle and/or the immune cycle of the subject; and an output component for outputting the immune status or periodicity of the immune cycle, the immune cycle of the subject and/or the future status or immune cycle of the subject.

The present invention takes into account a subject's physiological data as part of a method and system providing analysis and interpretation of obtained data and outputting that data to the individual and or their adviser, trainer, coach, doctor or any other relevant individual to provide information about their immune status, cycle for their consideration and/or providing recommendations relating to the immune status or cycle for planning or undertaking activities to improve health, wellness and performance of an individual, maximizing recovery and lowering/mitigating detrimental outcomes such as long recovery times and ineffective or suboptimal vaccination events or risks of injury or delayed recovery from injury or minor insults such as training, overtraining, overexertion, stress or sleep deprivation. The output may take the form of a report that may be printed or displayed on a screen.

The future status is typically the subject's predicted status in the next 1-10 days or the subject's next predicted immune cycle and as a result of knowing the future status, the subject or any other relevant individual can make a decision or lifestyle choice based on that information.

While it is not possible to control all potential relevant immunological events or triggers such as exposure to infection and accidental injuries, the system and method of the present invention is applicable to circumstances which can be controlled and synchronized with the immune system. Examples include the timing of preventative vaccinations or exposure to physical insults or injuries such as those incurred as part of actions or an action plan including taking of supplements physical exertion, a training regimen, including sport training, rehabilitation, physiotherapy, elective or non-urgent surgery, and/or other potential insults such as stress or sleep deprivation.

Preferably, the processing component further includes an inference engine to compare the immune cycle and/or status of a subject with an activity database and generating a recommendation for an activity for the subject at a particular time with respect to the individual's current immune status and or predicted future immune status based on knowledge of their immune cycle.

According to a second aspect, the present invention provides a system for improving a subject's physiological response to an activity, the system including: an input component for obtaining data relating to the activity and/or the subject; a sampling component for obtaining physiological data from the subject; a data storage component for storing the physiological data obtained from the subject; a processing component to analyse the physiological data thereby determining on that basis the periodicity of the immune cycle and/or status of the subject; and an output component for outputting the periodicity of the immune cycle, the past and future immune cycle and status of the subject and the current or future status of the subject's immune system and/or cycle.

The present invention takes into account a subject's immune cycle as part of a method and system providing analysis, reporting and or interpretation of obtained data for output and consideration in undertaking an action or devising action plans in the form of recommendations to improve performance and health of an individual, maximizing recovery and lowering or mitigating detrimental outcomes such as injury or delayed recovery. Advantageously, the present invention may be used to improve a subject's physiological response to an activity in a number of fields including sport, fitness, medicine, aesthetics, health and well-being and preventative interventions. The present invention may have applications to individuals, teams or groups of individuals such as elite athletes, professional and semi-professional athletes, amateur athletes, health and fitness enthusiasts or individuals concerned with their well-being, performance and recovery from activities and injuries including surgery.

Preferably, the processing component further includes an inference engine to compare the activity data and the immune cycle and/or status of subject and generate an individualised recommendation for the subject.

The activity may include one or more of a training schedule, fitness regime, vaccinations, rehabilitation, elective or non-urgent surgery, diet and dietary intake, intake of supplements, intake of medications that modulate the immune response, lifestyle decisions and stressful activities such as sleep deprivation or overexertion that would at a particular time with respect to the immune status elicit an unwanted or heightened immune response.

Recommendations may include but are not limited to optimal time(s)/days for undertaking certain activities. One embodiment of a recommendation with respect to training and/or exercise may include when to undertake an activity and the intensity of training activity to be undertaken on a particular day (for example, loading). Loading generally means increasing one or any combination of volume, frequency, intensity and unloading means decreasing one or any combination of volume, frequency intensity of an activity. Further, recommendations may include rest and recovery measures or activities. For example, ice bath, massage, meditation supplement and/or nutrient intake, medicinal intake such as anti-inflammatories, hydrotherapy, aerobic activities, physiotherapy and other muscular skeletal therapies. Further recommendations with respect to lifestyle decisions may include providing information or advice on the impact of certain activities such as sleep where sleep deprivation at certain times may be more stressful, have a greater impact or time to recover than at other times.

Preferably, the input component further obtains data related to the day of an activity such that the inference engine compares the timing of the activity, the activity data and the immune cycle and/or status of subject and generates an individualised recommendation for the subject.

For example, an athlete may schedule a sporting event on a particular day and the action plan may include a modification that requires them to be able to perform at an optimal level on the specified date and the recommendation may be to rest on the preceding day despite the subject's immune cycle status being in an optimal loading phase. Examples of training and/or health fitness activities may include walking, jogging, sprinting and weight training. A recommendation may be to increase or decrease intensity and or duration of such activities. Another recommendation in response to activity data may be to optimise benefits from supplement and or nutrient intake such as at a time when there is likely to be a higher demand for their intake such as in the pro-inflammatory phase of the immune system.

In addition, where the activity is elective or non-urgent surgery, a recommendation is generated as to when to have elective or non-urgent surgery or when to avoid having surgery since there is variability in the response to such interventions. Similarly, for preventative vaccinations recommendations may be provided as to optimal times for heightened immunological response. The status of the immune system, whether in a pro-inflammatory state or anti-inflammatory state will impact on the efficiency of certain endeavors such as vaccinations, the recovery from injury or insult as a consequence of training, overtraining or surgery. Advantageously, the knowledge of the immune status enables recommendations based on the obtained and analysed activity and or physiological data so that actions are undertaken so as to optimise, maximise or improve the beneficial outcomes and/or minimise, avoid or manage (for example, by medication) the unwanted or detrimental outcomes such as a prolonged recovery period.

In an alternative, the processing component further includes an inference engine to compare the immune cycle and/or status of subject and generate a recommendation for the subject. Advantageously, this is a recommendation which does not make reference to activity data and the user need not specify the activity to undertake. In this case, the subject determines their immune cycle and status and the system and method of the present invention provides a list of recommendations of possible activities that can be carried out (or should not be carried out) based on the status of the immune system and/or cycle.

Preferably, the input component further obtains anthropometric and biometric data relating to the subject and/or activity. The input component may further obtain data relating to nutritional intake, preferences and lifestyle habits (i.e. height, weight, age, smoking status etc.) from the subject so as to provide more comprehensive recommendations for action plans.

Preferably, the physiological data includes an immune system marker, surrogate biomarker or characteristic by which the immune cycle and/or status can be identified such as basal or resting temperature.

Preferably, the recommendation provides information related to carrying out the activity, avoiding the activity, postponing the activity for a period of time or hastening the activity (i.e. a recommendation to do the activity tomorrow instead of the next day).

Preferably, the recommendation provides information related to the intensity, duration of physical exertion or social lifestyle activity such as sleep deprivation (e.g. more severe consequences from a late night and a longer recovery time).

Preferably, the immune cycle and/or status is determined by serial time dependent variations in the physiological data.

Preferably, serial time dependent variations in the physiological data includes at least two or more instances of physiological data to determine the immune dynamics and immune status of the individual. With two measurements, an increase or decrease in the immune markers can be determined. If not, three or more measurements may be needed. The immune cycle may be determined by obtaining three or more instances of physiological data over a sufficient time period to resolve the dynamics and periodicity of the immune cycle.

For example, the immune status determined by obtaining two or more instances of physiological data over a sufficient time period may resolve whether the individual is in a pro-inflammatory state as seen by the marker rising or in an anti-inflammatory phase of their immune cycle, as seen by the marker decreasing.

Two serial measurements can give status, that is rising markers indicate a pro-inflammatory phase, decreasing markers indicate an anti-inflammatory phase. Three or more serial measurements are required to determine the cycle (i.e. to determine at least a trough or a peak). For one-off activities such as vaccinations or single stress events, status information may be sufficient information whereas regimens or long term planned activities may require cycle related information.

Preferably two, three or more serial daily or near daily (such as every second day) measurements of physiological data are taken from the subject in order to accurately resolve the immune status or cycle, its periodicity and amplitude. The frequency of the physiological data taken will depend on the variable that is being measured. If blood samples are used, the samples could be taken every day or second day or three times a week as practical or convenient to take samples. With finger prick blood samples, it may be convenient to take samples more frequently. In the case of temperature, any number of samples may be taken—particularly if a sensor device is worn on the subject. Preferably, the sample and data is taken/obtained at the same time of the day and in the same physical state, e.g. resting, so as to avoid confounding variables relating to non-immune related variations and known diurnal variations. As an example preferable data for temperature is a basal or resting measurement at the same time of the day.

The sampling component may include one or more devices which measure physiological information. Preferably the sampling component includes but is not limited to one or more of a contact or non-contact temperature sensor, a blood sampling device, blood biomarker sensor, blood testing unit or salivary collection unit, urine or sweat sensing and monitoring devices for surrogate markers such as blood pressure monitors and heart rate monitors.

In an alternative, the sampling component may be an input device to receive manually entered parameter(s). The parameter(s) may be the temperature of the subject or any parameter which is easily measured or obtained by a subject. For example the subject may input the results of their blood test, biomarker level, temperature, blood pressure and or heart rate.

According to a third aspect, the present invention provides a method for determining the immune status or immune cycle in a subject, including the steps of: obtaining physiological data from the subject; analysing the physiological data and thereby determining the immune status and/or cycle of the subject; and outputting the immune status or periodicity of the immune cycle, and the immune cycle of the subject and/or the future status or future immune cycle of the subject.

According to a fourth aspect, the present invention provides, a method for optimizing a subject's physiological response to an activity, in a subject, including the steps of: obtaining data relating to an activity and physiological data from the subject; and making one or more recommendations based on the activity and the subject's current or future status in their immune cycle.

Preferably, the future immune status and immune cycle is determined by using the method of according to the third aspect of the invention.

According to a fifth aspect, the present invention provides a method for improving a subject's physiological response to an activity, including the steps of: obtaining data relating to the activity; obtaining physiological data from the subject; analysing the physiological data and thereby determining the immune cycle and/or status of the subject; and the method further includes the step of making recommendations based on the activity data and the subject's current or future status in their immune cycle.

Preferably, the method further includes the step of comparing the activity data and the immune cycle and/or status of the subject to generate one or more recommendations based on the combination of the physiological data and activity data. The activity or action plan may be any one or more of training, rehabilitation, elective and non-urgent surgery, well-being and health, lifestyle or vaccinations decisions.

The present invention takes into account a subject's immune status and cycle as part of a method and system providing analysis and interpretation of obtained data and reporting for consideration in undertaking an action or devising an action plan or recommendation to improve performance, health, maximize recovery and lower/mitigate detrimental outcomes such as injury or delayed recovery of the individual. Whilst some environmental factors that are known to impact on the immune system are unpredictable (i.e. exposure to infection, viruses, injury), a subject using the system and method of the present invention may take measures to mitigate the risk of infection or injury by avoiding loading, overtraining or overstressing the body (or limiting exposure to injury such as surgery or infections/sick people) at a less optimal time for the individual's body/immune system to deal with such issues by immune synchronization.

Advantageously, the present invention utilises measurements of physiological data (e.g. biological markers and biometrics or variables or physiological markers) to enhance and improve the outcome of the planned activity and as a result the health, performance and recovery of a subject. The activities may include but not be limited to training which itself includes recovery, loading, unloading, tapering, injury prevention, injury management, injury treatment, athletic maintenance, overtraining prevention, longevity of athletic performance, and/or to mitigate risk of injury or prolonged recovery. In a group setting, such as in a team or squad, the information may be used by the individual, coach or team leader. It may also be used by the coach to select athletes to perform or not. Advantageously, these measures will prevent overtraining, increase longevity and performance of the athlete and/or mitigate the risk of preventable injury or prolonged recovery as well as providing data to assist in the more informed selection of an athlete or team for an event.

In an embodiment of the invention, the action or action plan is synchronised and tailored to the subject's own immune status or cycle. The action plan may encompass a training plan, rehabilitation plan, general health or wellness plan which assists to improve health and wellness including optimising beneficial activities such as intake of energy, immune or vitamin supplements, meditation and other recovery processes and timing of exercise, and minimising exposure to adverse or detrimental insults such as sleep deprivation, over-exertion or risk of exposure to infection. The action plan may include meal types (patterns and quantities), intake of energy, immune or vitamin supplements, meditation and other recovery processes and timing of exercise. The recommendations for the action plan provided by the system and method of the present invention will advise or recommend when a subject undertakes certain activities such as those mentioned above with respect to their immune status or cycle so as to improve the benefits of such actions. For example, performance, health, well-being, mitigate chance of injury, assisting with injuries resolving or healing and assisting with recovery. Further, such recommendations may include not taking actions such as consuming supplements at a time when they will not be of maximum benefit and thereby save on costs of such supplements for the individual and/or the team.

The action plan may include training to increase physical attributes such as strength, muscle mass, speed, endurance, flexibility, explosiveness and the like and may also incorporate a number of factors including loading, unloading, rest, nutrition, recovery methods such as massage, hydrotherapy, meditation physiotherapy and other muscular skeletal therapies and others known to those skilled in the art. Additionally, the activity may relate to a training, rehabilitation plan which may be better tailored to avoid overtraining, injury, immune depression, risk of infection, and psychological burnout. Further, the action plan may include recommendations for optimal times for vaccinations and/or elective non-urgent interventions or surgery or elective medical procedures. Further, if the individual has knowledge of their immune status, the action plan may include recommendations for improving or optimising recovery from unavoidable or unplanned insults or injuries i.e. as a result of participating in a scheduled sporting event based on their status at the time of the event and potential injury. Such recommendations may include but not be limited to the taking of nutritional supplements or immune modulating medications such as anti-inflammatory medications based on when in the subject's immune cycle or status the insult or injury was sustained or is likely to be sustained.

The present invention identifies a subject's personal immune status or cycle by obtaining physiological data from the subject. From this data the periodicity of the immune cycle can be established if sufficient measurements are taken. This enables ascertainment of the dynamics of the individual's immune cycle, the individual's current immune status as well as prediction of the cycle to identify the subject's immune status, that is, where a subject is going to be in their immune cycle in the near future. The system and method of the invention makes recommendations to improve/optimise outcomes of certain activities by correlating the activity data with the individual's present and or predicted status in their personal immune cycle. For instance, if it is known that a subject's immune status in their cycle is going to be at point X in two days and we know that for the specific activity rest is best suited at point X then the system will make a recommendation to the individual to rest.

Furthermore, the invention can detect early changes in the immune system such as subclinical manifestations of an infection or disease that the individual may not be aware of or be able to identify by detecting when an individual's immune system is outside of (above) normal or acceptable levels for the subject and may recommend a change to the planned activities, training regimen action plan based on the inputted physiological data. Monitoring immune markers or surrogate immune markers such as sub-clinical temperature rise, increased blood pressure or heart rate can give an early indication of an infection or underlying undiagnosed disease.

The system or method of the invention may further identify when a subject's data is not tracking according to their cycle or is outside of usual or normal parameters, giving an indication (early) that something is happening e.g. imminent or oncoming infection, sub-clinical injury or abnormal physiological state such as nutrient exhaustion, metabolic overload, overtraining etc. As a result the subject may be advised to seek measures to rectify abnormality such as rest, seek medical attention, take supplement, avoid exposure to risk factors such as exposure to infection or immune activities such as sleep deprivation and stress. Advice may be provided by the system as an alert to stop following the previously generated action plan and or be provided with an updated version of their action plan.

Advantageously, in the context of an action plan with respect to training, rehabilitation and physiotherapy, the present invention may provide recommendations that (i) improves a subject's ability to adapt to physical loading; (ii) optimises a subject's ability to recover from physical loading, (iii) determines periods where a subject should be cautious of the intensity, frequency, volume (and other factors associated with physical loading) utilised to physically load and/or unload, (iv) determine periods where a subject should refrain from physical loading; and (v) determine periods where a subject's response to recovery methods are optimal.

In the context of an action plan with respect to health or wellness the present invention may provide recommendations that include but are not limited to (i) optimising a subject's action plan with respect to preventative interventions such as vaccinations, non-urgent surgery, the taking of supplements and nutrients, medications, avoidance of risks such as infections or injuries, sleep deprivation, over-exertion and other stressors.

Preferably, the analysis of the subject's immune cycle and status is carried out before any activity is commenced. Advantageously, in the context of a health plan, the present invention may provide recommendations that (i) optimizes the subject's ability to respond to a vaccine (ii) optimizes a subject's ability to recover from surgery (iii) optimizes when to take compositions for nutritional supplements (iv) optimizes the subject's ability to respond to rehabilitation and physiotherapy and other recovery measures including medication and (v) provide insights into underlying undiagnosed disease.

The present invention uses knowledge of an individual's immune status or immune cycle obtained by analysing serial measurements of biomarkers to provide predictive analytics and recommendations for the management of activities tailored to the individual.

BRIEF DESCRIPTION OF DRAWINGS

The invention will now be described in further detail with reference to the accompanying drawings. It is to be understood that the particularity of the drawings does not supersede the generality of the preceding description of the invention.

FIGS. 4a to 4e illustrate capture and prediction of physiological data relating to the immune cycle;

FIGS. 5a to 5g are graphs of biomarker data of individuals;

DETAILED DESCRIPTION

Definitions

Figure 1:
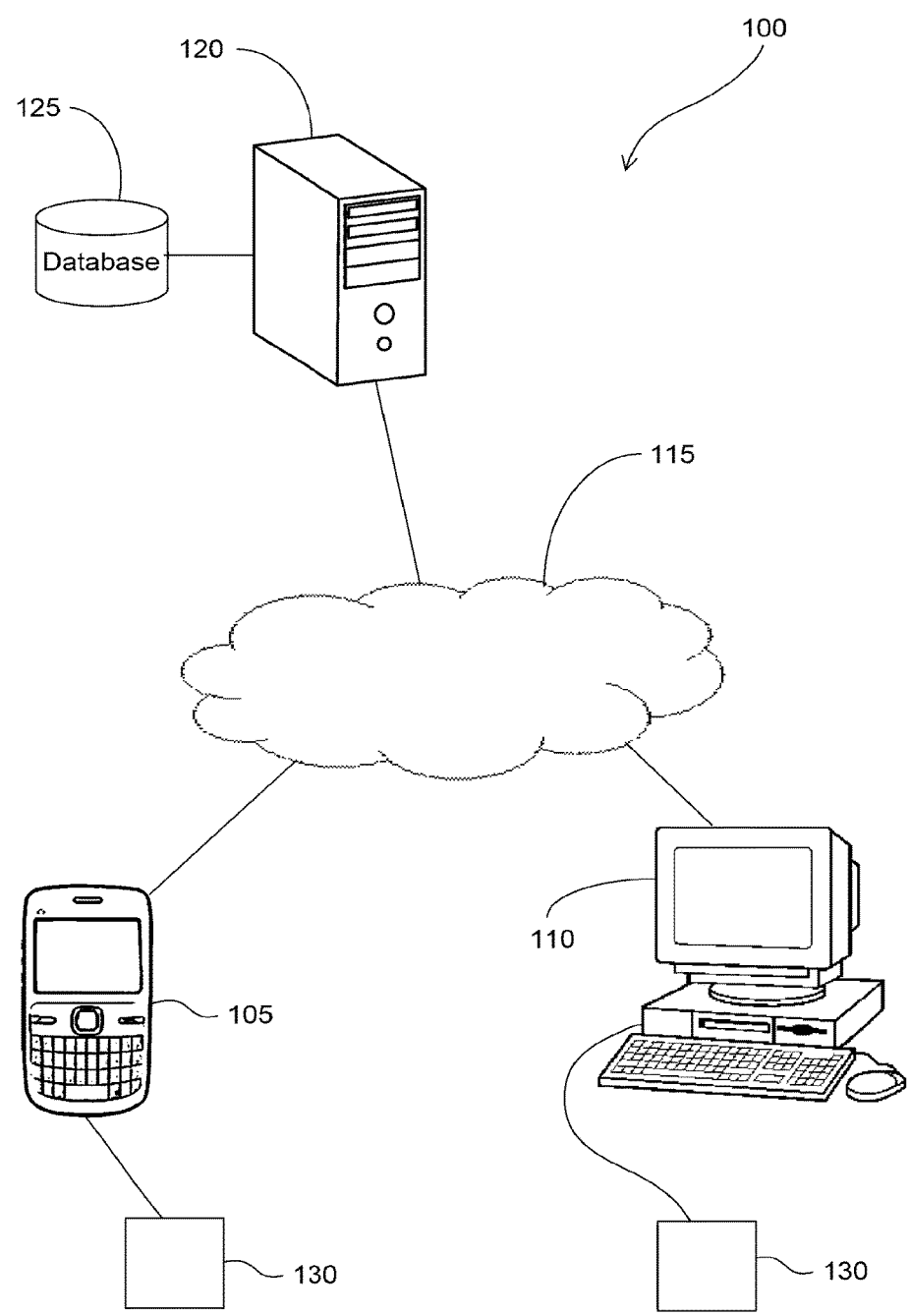
FIG. 1 is a schematic diagram of an example network that can be utilised to give effect to a method and system according to an embodiment of the invention.

Serial measurements mean taking two or more measurements of physiological data to determine the immune status and or the immune cycle dynamics of a subject.

Activities include measures undertaken for the purpose of sustaining or improving health, wellness, fitness and/or physical capabilities or performance. Activities further include measures that may impact on the immune system including either by provoking an immune reaction such as a vaccination, injury, insult or by leading to immune suppression such as overtraining or stress.

Activities include the following non limiting examples:

Training, exercise or other activities which require or enhance physical activity including strength and performance, plastic or cosmetic surgery which is undertaken to enhance appearance and thus provide both physical and psychological well-being, non-urgent medical interventions such as hip and joint replacements which enhance physical mobility and reduce pain.

Dental procedures which include extractions, root canal treatments and cleaning performed by a suitably trained individual to improve and prevent pain and suffering.

Preventative vaccinations which enhance resistance to or prevent illness or disease as a result of infections.

Rehabilitation and/or recovery measures including medication which enhance recovery from insults or injuries.

Further, the activity may form part of a regimen, prescribed plan, routine or other repeated process or may be a one-off or irregular event such as a surgical procedure or vaccination, where such activity has or may have immunological or immune response provoking consequences.

Recommendation and or advice and or action plan relates to the activities that trigger an immunological event and means:

An exercise or training plan and/or schedule such as those commonly used in the general fitness or sports industries for individuals interested in improving their health and/or physical capabilities whether that individual is a recreational exerciser (gym user, runner, martial artist etc.), a development or elite athlete, professional performer (actor, dancer etc.) or performs other activities that involves intense physical exertion (military personnel, labourers, construction workers, etc.).

A schedule or advice for undertaking elective or non-urgent medical interventions including surgery, dental procedures or other means of treatments whether for health, aesthetic, cosmetic or other non-urgent interventions;

A schedule or advice for undertaking rehabilitation to be utilised by individuals or professionals seeking to improve biomechanical function A schedule or advice for measures related to well-being and health including:

A nutrition or dietary plan for improving or optimising the benefit from the intake of foods, supplements, vitamins etc. For example, supplements will be most useful and beneficial when the body is most in need of such supplements. In this instance such times are times of increased demand such as during the active or pro-inflammatory phase of the immune cycle rather than the anti-inflammatory or quiescent phase.

Recommendations for taking immune modulating medication. For example, anti-inflammatories may be indicated when there is likely to be an unwanted heightened immune response.

Recommendations for lifestyle or social activities which may provide stress such as sleep deprivation and/or physical over-exertion ("stress or rest" notion).

Recommendation for timing of preventative vaccination.

The recommendations or action plan based on the immune status or cycle may be specified by the system as a result of the input of activity data. Alternatively, the system may specify a number of recommendations which can be selected by the user. Further, the recommendation or action plan may include advice to undertake or avoid undertaking a particular activity at a particular time in their immune cycle.

An improved physiological response means a response to one or more of the activities described in the recommendations or action plans above. Improved response depends on activity. For example, an improved response is a heightened response for a vaccination event whereas an improved response is a dampened response after surgery to lessen recovery time.

Health, wellness and well-being means promoting well-being or wellness including attaining an enhanced state of physical or psychological well-being.

Individual(s) means: a subject that performs or seeks to perform an activity and includes a single individual or an individual who is a part of a group or team of individuals including elite athletes, professional and semi-professional athletes, amateur athletes, health and fitness enthusiasts or individuals concerned with their well-being. Individuals may include individuals that are a part of teams such as football teams, basketball teams or other groups such as military personnel and police and other bodies that rely on the efforts of more than one individual for an outcome.

Individuals or subjects include animals and or mammals, including but not limited to a human, horse, dog, cow, cat, and may, where appropriate, be used interchangeably with the term "individual" or may include a team of individuals.

Insult or injury includes physiological damage, muscle damage, skeletal damage, resulting from an activity and may have a consequence including but not limited to symptoms such as soreness, fatigue, lactic acid build up, or other by-product of the activity. A vaccination is similarly something outside "normal" daily activity and has a consequence. In this instance, to stimulate the immune system and may produce ultimate beneficial consequences such as protection from infection but also produce symptoms such as soreness, fatigue and malaise. Surgery, albeit for beneficial outcomes, is similarly not a normal activity and does have consequences including soreness, fatigue and recovery times which vary between individuals. All these activities are usually undertaken for a beneficial outcome and are usually by choice rather than necessity, that is, are not urgent or life-threatening and all are usually associated with desired outcomes and are known to have effects requiring "recovery" to a "normal" or optimised or enhanced level of wellness, fitness or heath.

Insult or injury includes injuries resulting from unavoidable or unplanned events or activities such as car accidents, life-saving surgery, or events whose scheduling is outside the full control of the individual and reliant on the availability of others and include elective surgery or dental interventions. Insults or injuries also include preventable injuries. Preventable injuries mean injuries suffered as a consequence of actions that could have been avoided. For example, overtraining and resulting injuries which include muscular injuries as well as symptoms such as fatigue, malaise, exhaustion, burnout, immune suppression and prolonged recovery time. Preventable injuries also include sleep deprivation or physical overexertion or stress.

Normal or non-diseased includes individuals from the general population who are otherwise not recognised as having serious or chronic illnesses such as cancer, autoimmunity, chronic infections or other serious illnesses. While being overweight or obese is common, it is not generally considered a serious disease unless an individual is morbidly obese. Similarly, aches and pains which may be attributable to arthritis are not considered serious illnesses until they result in impediment of normal activities and require medical interventions.

Training means: perform or omitting from performing an activity and includes but is not limited to recovery, loading, unloading, tapering, or unchanging or static level or intensity of activity, injury prevention, injury management, injury treatment, athletic maintenance, overtraining prevention, management of athletic performance, and or mitigation of risk of injury or prolonged recovery. Such terms are familiar to those skilled in the art of training.

Loading means: increasing one or any combination of volume, frequency, intensity.

Unloading means: decreasing one or any combination of volume, frequency intensity of an activity.

Throughout the specification, the term "Normal Body Temperature" refers to normal body temperature that is generally accepted to be 37.0° C. but may vary between 36.1° C. and 37.2° C. and still be considered normal. Variations in normal body temperature can result from activities such as exercising, smoking, eating and drinking. Further, an individual's normal body temperature is usually lower in the morning compared to the afternoon due to the low level of activity in the early hours of the morning. Other variations in normal body temperature may be attributed to the location from which the temperature is taken. Three common ways to ascertain an individual's body temperature using standard contact thermometers are oral measurements, rectal measurements and axillary measurements. Normal oral measurements are reported to range between 35.99° C. to 36.99° C. which is 0.5° C. lower than rectal readings but generally 0.5° C. higher than axillary measurements. Other devices for taking an individual's temperature from other locations may include wearable patches, ingestible devices and non-contact thermometers (such as infrared thermometers).

Preferably, in order to ascertain the serial fluctuations in an individual's temperature associated with the immune cycle, the measurements are taken from the same location of the body and preferably using the same device. Using the same device will overcome variations associated with differences in specifications and sensitivities between devices. Preferably, the measurements are taken to determine basal temperature or resting temperature and are taken at the same time of the day preferably before rising or are monitored continuously.

Throughout the specification, the terms "cycling" or "cycle" or "immune cycle" or variations thereof refers to a repetitive oscillation of an immune biomarker. The cycle is sinusoidal-like and the period of the wave is the time it takes to complete a cycle (i.e. in the present case, the length of time of one point in the wave of the cycle to the corresponding point in the next wave). It will be appreciated that measurements taken over half a period may be sufficient to determine the periodicity of the immune cycle in a subject. It will be appreciated that two measurements of a biomarker may be sufficient to determine the status, such as pro-inflammatory or anti-inflammatory state, of the individual which may suffice in some instances when knowledge of the periodicity of the cycle or future prediction of immune status is not required.

For example, the cycle biomarker changes periodically from a maximum to a minimum and back to a maximum over a given length of time which is typically about 3 days to about 15 days, more typically about 7 days to about 14 days, depending on the biomarker and the individual.

Throughout the specification the term "immune system marker" generally refers to any molecule or factor which provides an indication of the state and/or activity of the immune system. These markers may be directly linked to specific components of the immune system e.g. linked to the innate immune system which includes but not limited to markers of inflammation such as CRP, ESR and temperature. Other innate system markers may include complement factors such as C3 and C4 and or innate cellular markers such as markers and/or numbers of macrophages and polymorphonuclear (PMNs) cells, neutrophils and eosinophils and basophils (collectively polymorphonuclear (PMNs) cells). Biomarkers of the adaptive immune system include markers of T and B cells such as CD8 positive, CD4 positive and/or markers of specialised subsets such as CD38 and IgD. Biomarkers may also include cytokines which may be produced by components of both the innate and adaptive immune system. These include but are not limited to IL2, IL6, IL10, TGF-beta and Interferon-gamma. Any biomarker that provides a more general indication of the overall status of the immune system is a suitable marker. Examples of suitable immune system markers include acute phase inflammatory markers such as C-Reactive Protein and serum amyloid A. Immune system markers include surrogate markers or physiological markers which result from systemic manifestations of the immune system and include temperature, heart rate and blood pressure.

Throughout the specification, the term "monitoring" or serial measurements or variations thereof refers to the analysis of the levels of a biomarker over a sufficient period or length of time to suitably characterize the periodicity and or dynamics of the immune cycling or immune status of the immune system. Other indicators of the immune status or cycle may include the rate of the increase or decrease to reach the peak or the nadir in the amount and/or level of the biomarker. Examples of suitable monitoring times and frequency of analysis are described herein. Generally, the monitoring or analysis will be performed on samples obtained from the subject. However, in some instances the monitoring or analysis will be performed directly on the subject, such as the determination of body temperature.

Throughout the specification, the term "sample" refers to a material containing the biomarker. The sample can be used as obtained directly from the source or following at least one step of (partial) purification. The sample can be prepared in any convenient medium which does not interfere with the method of the invention. Typically, the sample is an aqueous solution or biological fluid as described in more detail below. The sample can be derived from any source, such as a physiological fluid, including blood, serum, plasma, saliva, sputum, buccal swab, sweat, urine, milk, mucous, synovial fluid, transdermal exudates, pharyngeal exudates, bronchoalveolar lavage, tracheal aspirations, semen, cervical mucus, vaginal or urethral secretions and the like. Preferably, the sample is blood or a fraction thereof. Pre-treatment may involve for example, preparing plasma from blood, diluting viscous fluids, and the like. Methods of treatment can involve filtration, distillation, separation, concentration, inactivation of interfering components, and the addition of reagents. The selection and pre-treatment of biological samples prior to testing is well known in the art and need not be described further. In some embodiments, due to current technology, a drop of blood from a finger prick will be a sufficient sample. For example, testing acute phase inflammatory marker levels.

It will be appreciated that the definitions provided above are non-exhaustive.

Surprisingly, the inventors have found that serial measurements of the basal and/or resting temperature of a subject is also a good marker of the immune cycle and/or status in an otherwise healthy non-chronically diseased individual. Temperature is known to be associated with inflammation and thus an indicator of immune activity in the disease state, e.g. it is known to rise during an infection. It is also a known indicator of the fertility cycle in females. Further, it also known to have a diurnal rhythm with variations occurring at different times of the day and after different activities. Surprisingly, we have found, and it has not previously been known that temperature is an indicator of the immune cycle and status. It has not previously been known to be an indicator of immune cycle or status in healthy non-chronically diseased individuals. In one embodiment, the basal body temperature of an individual is recorded on a daily basis. In another embodiment, a sampling component or device may be worn by a subject and the sampling component constantly monitors temperature and sends it to a server which determines the immune cycle or immune status.

In another embodiment, a sampling component may be worn by a subject, and the sampling component is a device which constantly monitors temperature and sends it to the server. Other examples of non-invasive monitoring of any of the biomarkers of the immune system use similar technology such as those applied to other blood components such as blood oxygen levels and glucose or known technologies which measure heart rate and or blood pressure.

It will be appreciated that the present invention may be used in any field where an improved physiological response to an activity is desirable and uses an individual's immune cycle and status as a guide. In one aspect, the present invention may be used in a gymnasium, training facility, medical facility, outdoors or at a user's home in conjunction with for example, a fitness regimen to improve health by undertaking exercise. The invention may also be used in conjunction with physical exercise for rehabilitation, that is, used by physical rehabilitation services that aim to help a subject improve or regain body function due to a medical condition, injury, trauma or insult. The system and method of the present invention may be used in rehabilitation to recover from serious medical conditions, diseases, injury, trauma or insult (i.e. spinal injury, loss of limbs, heart attack, brain injury, stroke etc.). In another aspect, the present invention may also apply to general health and lifestyle activities so as to assist a subject with recommendations based on their immune cycle and status. Another lifestyle activity for example, relates to optimising sleep patterns and times, meal types, patterns and quantities, optimal intake of energy, immune or vitamin supplements, medications, advice as to when to avoid potentially detrimental activities such as lack of sleep and overtraining, and other stressful activities or stressors. Further, it may provide advice as to when to undertake potentially beneficial activities such as rest, recovery processes such as ice baths, medication, massage and meditation. Further, the system and method of the present invention may advise when to avoid certain activities which may be beneficial at one point in the immune cycle but detrimental at others and vice versa.

The present invention may be used in sports training and or sports events, rehabilitation (from injury or insult) such as (i) professional and amateur sports competitions (whether team or individual), (ii) team or individual practice sessions to further develop physical skills, improve physical attributes, or prepare for a competition, and/or any team or individual physical workout, physical exercise, athletic conditioning or training session (whether or not in preparation for a competition), (iii) an entertainment activity involving physical exertion (iv) any activities conducted for personal fitness, development of physical attributes, reduction in fat composition, or for personal health and well-being. The present invention may also be used to assist with the preparation and/or selection of an individual(s) or team members for an event or competition based on their immune status, that is, their position in their immune cycle. For example, selecting certain players or telling an athlete or individual how hard to push themselves on the day of the event based upon their status in their immune cycle at that point in time. Further, the training regimen or action plan may be synchronised with the date of an event e.g. plan a working or training regimen up to an event (e.g. make sure that the rest period coincides with the pre event preparation). The immune cycle and status will help determine the athlete's or individual's response to an activity. In one aspect, knowledge of the status of the individual with respect to their immune cycle will indicate the potential for exertion and or level of activity to be undertaken or exposed to in order to avoid prolonged recovery or injury following the event.

Embodiments of the present invention can be realised over a network 115, an example of which is shown in FIG. 1.

FIG. 1 illustrates a distributed system 100 for improving a subject's physiological response to an activity. The system 100 obtains physiological data from the subject and processes the data to determine the immune cycle and/or status of the subject. The system 100 for improving a subject's physiological response to an activity and the health of a subject may run on a network 115 which includes one or more electronic devices 105, 110 and one or more server processing systems 120.

The electronic devices may be connected to one or more sampling components 130. The electronic devices include one or more mobile communication devices 105 and one or more personal computers (PCs) 110. The sampling components 130 measure and obtain physiological data of the subject, or the subject may enter the physiological data manually, or another party may enter the physiological data into the system (i.e. the doctor, trainer, coach, nurse, adviser etc). The obtained physiological data is communicated via a wide area communications network such as the Internet 115 to a server processing system 120. The sampling components 130 measure physiological data in a subject and may include for example temperature measurement devices (wearable sensor or a thermometer for example), blood analysis devices (such as those which enable CRP, high sensitive CRP (hs-CRP) and Ultra-sensitive CRP (Us-CRP) tests, saliva sampling devices and the like.

The server processing system includes a server 120 connected to a database 125. The electronic device 105, personal computer 110 and server 120 are connected via a network 115 such as the internet. It will be appreciated that the sampling device 130 may not be required if data is directly inputted into electronic device 105, 110 by the user.

For example, the user may take their own temperature with a thermometer and input the results themselves into a smartphone application or a website or a piece of software associated with the electronic device 105, 110. Alternatively, another party may enter the physiological data into the system (i.e. the doctor, trainer, coach, nurse etc).

The transfer of information and/or data over the network can be achieved using wired communications means or wireless communications means. It will be appreciated that embodiments of the invention may be realised over different networks, such as a MAN (metropolitan area network), WAN (wide area network) or LAN (local area network). Also, embodiments need not take place over a network, and the method steps could occur entirely on a client or server processing system. For example, a device may include a combination of a sampling component and electronic device, such as a wearable computer with a sensor (i.e. a watch with an inbuilt thermometer or the like, Fitbit™/Jawbone™ UP, Olive™, Duofertility™), under the skin chip implant, an ingestible pill that measures temperature such as the CorTemp Ingestible Core Body Thermometer Pill and the like. It will be appreciated that the sampling component may form part of an overall device which includes a combination of a sampling component and electronic device as well as the processing component to complete the analysis. The sampling component may also take the form of a normal contact thermometer or an infrared thermometer—in this regard, the thermometer may be used by the subject and the physiological data is inputted manually.

At the server 120, the physiological data is received or retrieved from the database 125, and analysed to determine the immune status or to estimate a periodicity of the cycling of the physiological data (which will be further described with reference to FIG. 3). From the estimated periodicity of the cycling of the physiological data, the server 120 then determines the subject's current status and/or future predicted status in their immune cycle. The system may then display the immune cycle and/or status so that a user may interpret the results. In an alternative, a recommendation may be made in relation to the activity and provided to the electronic device 105, 110 via the network 115. This will be described further with reference to FIG. 6. It will be appreciated that the physiological data and determined immune cycle and status that is obtained from the subject need not be seen by the subject and the information may be sent back directly to a user of the system (such as a coach or a doctor). Further, it will also be appreciated that the physiological data and determined immune cycle and status that is obtained from the subject may not be seen by anyone and output may just be advise or inform the user. In an alternative, the output may also be recommendations about what actions are best suited for a given day (as will be described further with reference to FIG. 6).

Figure 2:
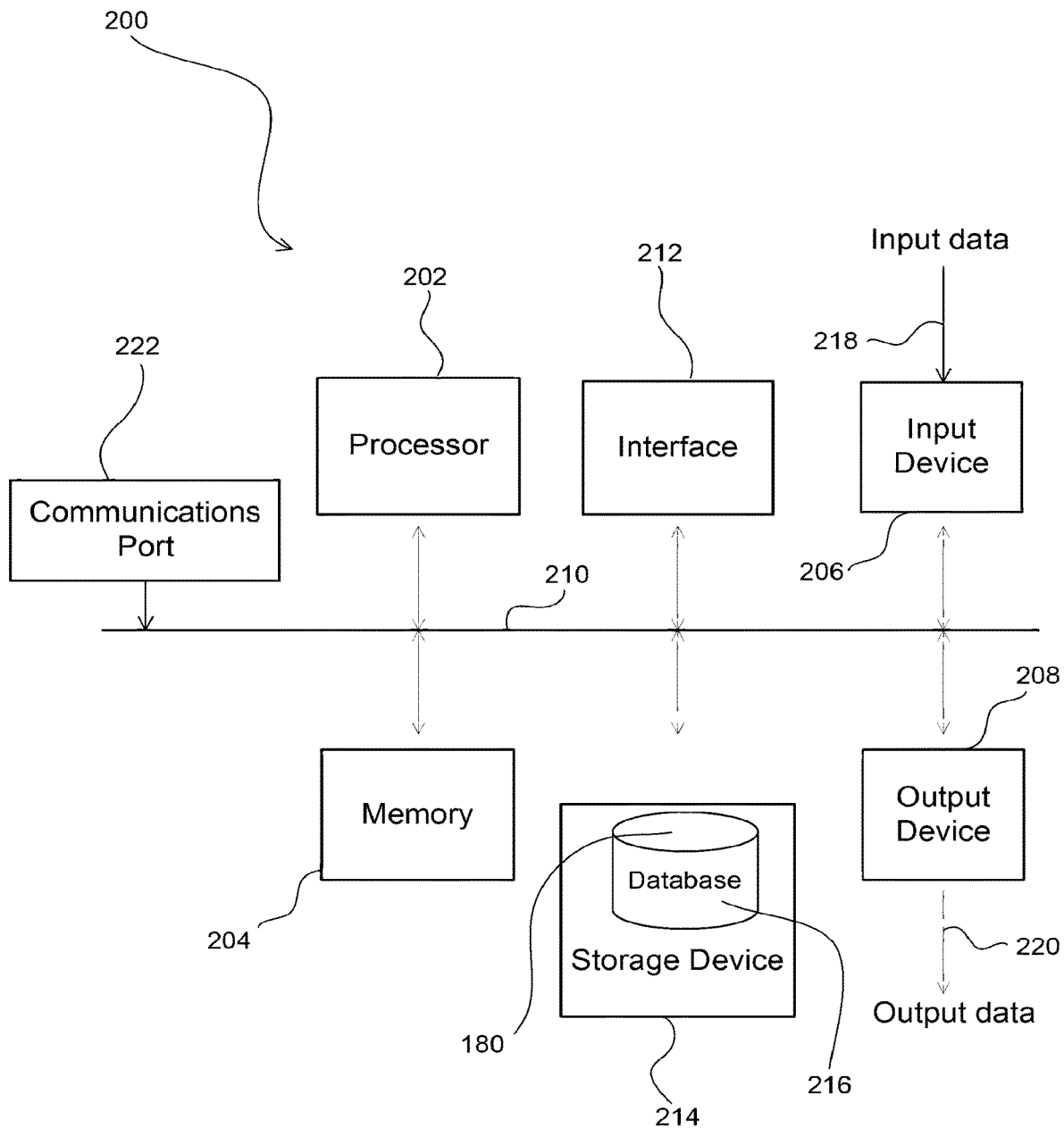
FIG. 2 is a functional block diagram of an example processing system.

The mobile communication device 105, personal computer 110, server 120, and sampling component 130 may include a processing system 200 shown in FIG. 2.

The processing system 200 includes a processor 202 (or processing unit), a memory 204, at least one input device 206, at least one output device 208 and a communications port 222. As is shown, the processor 202, memory 204, input device 206, output device 208 and communications port 222 are typically coupled together via a bus or group of buses 210. In certain embodiments, input device 206 and output device 208 may be the same device such as in the case of, for example, a computer graphics display or handheld device such as a tablet or mobile communication device that incorporates a touch-screen. In the case of sampling component 130 the input device may include a sensor to capture physiological data relating to a subject.

An interface 212 can also be provided for coupling the processing system 200 to one or more peripheral devices. For example interface 212 may include a PCI card or PC card. At least one storage device 214 which houses at least one database 216 can also be provided.

The memory 204 may include any suitable memory device and including, for example, volatile or non-volatile memory, solid state storage devices, magnetic devices, etc. The memory 204 may typically store an operating system that provides functionality to the processing system 200. A file system and files are also typically stored on the storage device 214 and/or the memory 204. The memory 204 may also include one or more software applications or program data.

The applications running in memory 204 may include a web browser or application suitable application for displaying electronic documents for reading or reviewing and accessing the network 115 to carry out the method and system of the present invention.

The processor 202 may include more than one processing device, for example to handle different functions within the processing system 200. Input device 206 receives input data 218 and may include, for example, a sensor, a keyboard, a pointer device such as a pen-like device or a mouse, a touch-screen, audio receiving device for voice controlled activation, such as a microphone, data receiver or antenna such as a modem or wireless data adaptor, data acquisition card, etc. The input device 208 may be operable by a user to enter input data 218, or it may receive data from another input data source. Thus, the input data 218 may be provided by different input devices 206. For example, in an embodiment the input data 218 may include keyboard or mouse instructions entered by a user, in conjunction with data received via a network. Preferably, the input device 206 includes a touch screen associated with an electronic communication device.

Output device 208 produces or generates output data 220. In one embodiment, the output device 208 includes a display device (such as a computer graphics display) for providing output data 220 in a visual form. In another embodiment, the output device 208 includes a display device or monitor together with a set of audio speakers in which case the output data 220 may be provided in an audio-visual form.

It will be appreciated that other types of output devices 208 may also be used, such as, a port (for example a USB port), a peripheral component adaptor, a data transmitter or antenna such as a modem or wireless network adaptor, etc.

It will also be appreciated that the output data 220 could be output from a variety of different output devices 208 such as, for example, a visual display on a monitor in conjunction with data transmitted to a network. In such an embodiment a user may view data output, or an interpretation of the data output, on, for example, a monitor or using a printer.

The storage device 214 can include any form of data or information storage means, for example, volatile or non-volatile memory, solid state storage devices, magnetic devices, etc.

The communications port 222 allows the processing system 200 to communicate with other devices via a hard wired or wireless network, such as network 115 in FIG. 1.

In use, the processing system 200 can be adapted to allow data or information to be stored in and/or retrieved from, via wired or wireless communication means, in the at least one database 216. The interface 212 may allow wired and/or wireless communication between the processing unit 202 and peripheral components that may serve a specialized purpose. The processor 202 may receive instructions as input data 218 via input device 206 and can display processed results or other output to a user by utilising output device 208. Multiple input devices 206 and/or output devices 208 can be provided.

It should be appreciated that the processing system 200 may be any form of terminal, server processing system, specialised hardware, computer, computer system or computerised device, personal computer (PC), mobile or cellular telephone, mobile data terminal, portable computer, Personal Digital Assistant (PDA), pager or any other similar type of device.

Figure 3:
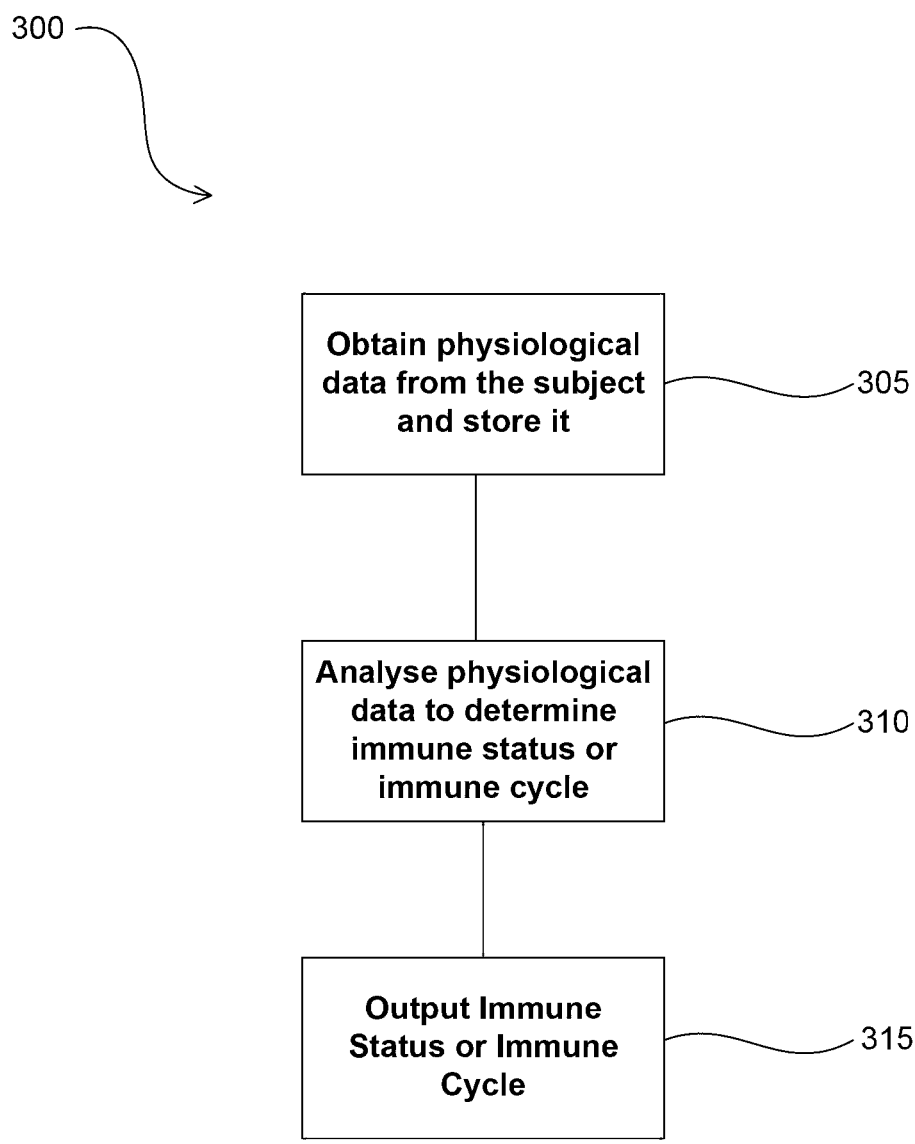
FIG. 3 a flow diagram illustrating an example method of the invention according to a first embodiment.

FIG. 3 is a method 300 of the present invention for improving a subject's physiological response to an activity.

At step 305 a sampling component 130 obtains physiological data from the subject and stores it on a database 125 via server 120. The physiological data may include a biomarker, biometric data, and the temperature of the subject or immune system markers for example. These may be obtained via various sampling devices, or, in the case of temperature for example, the temperature may be input manually by the subject or in the case of CRP the results may be input by the subject or their doctor (with respect to elective or non-urgent surgery for example).

Once the physiological data has been obtained, at step 310 a processing component within the server 120 analyses the physiological data to determine the immune status and or resolve the periodicity and or dynamics of the immune cycle of the subject. In particular, the server 120 then analyses the physiological data to estimate the status and or immune cycle which may include sending initial data before sufficient data to estimate the immune cycle has been inputted, that is, the initial data which may show an increase or decrease and therefore the immune status but not a complete cycle of the biomarker. At step 315, an output component within the server 120 sends the information relating to the immune cycle or status to the electronic device 105, 110 via the network 115.

At step 310, a user of the system may, through their expertise, make a determination as to whether or not the subject should carry out the activity so as to improve the subject's physiological response to the activity. For example, a user of the system may be the subject themselves and they may be determining, when to load with regards to training, whether or not to rest or "stress" such as have an early or late night that evening, when to take supplements, when to have a vaccination. Once sufficient data to determine the immune cycle is received, the system indicates that their immune cycle, if unperturbed, will be following a particular trend in the near future e.g. the next 1 to 7 days and therefore the subject can make a decision or lifestyle choice based on that information. The user of the system may also be a professional such as a doctor or coach who then advises the individual.

In an alternative, before step 305, data may be obtained from the user in relation to an activity. For example, the activity may be training, rehabilitation, elective or non-urgent surgery, general health and well-being or vaccination. This may be selected from a menu or similar or may be entered manually. The data relating to the activity may be obtained manually from the user or may be predetermined for a particular activity. For example, the activity may be a vaccination or pre-surgery or training system in which case the activity data may be predetermined. In any event, some data will be required to be input relating to the activity such as, for example, the type of exercise being carried out, the type of recovery measure being carried out, etc. The data at this optional step may be obtained via an electronic input device such as a keyboard via electronic devices 105, 110. In particular, the data obtained may relate to the activity (e.g., health regimen, surgery, rehabilitation) that the subject is participating in.

Anthropometric and or the individual's biometric data may be also obtained and may include the subject's weight, height and gender in addition to other information such as nutritional and dietary intake, age and lifestyle habits.

FIGS. 4a to 4d are graphs of the system 100 of the present invention to determine the immune cycle and/or status of a subject. The system 100 of the present invention is used preferably in anticipation of an activity that is to be carried out or, in the case of surgery or training in sports, may be also used after the activity has been carried out. Preferably, in these cases it is used both before and after the activity has occurred. Advantageously, the system and method of the present invention improves a subject's physiological response to an activity by ensuring that the activity occurs at an appropriate point in the subject's immune cycle. For example, in the context of an athlete participating in a sporting event it may be that they have completed a game on a Saturday, for example, and using the system and method of the present invention can determine whether or not it is appropriate to train on, for example, the following Monday.

Figure 4A:
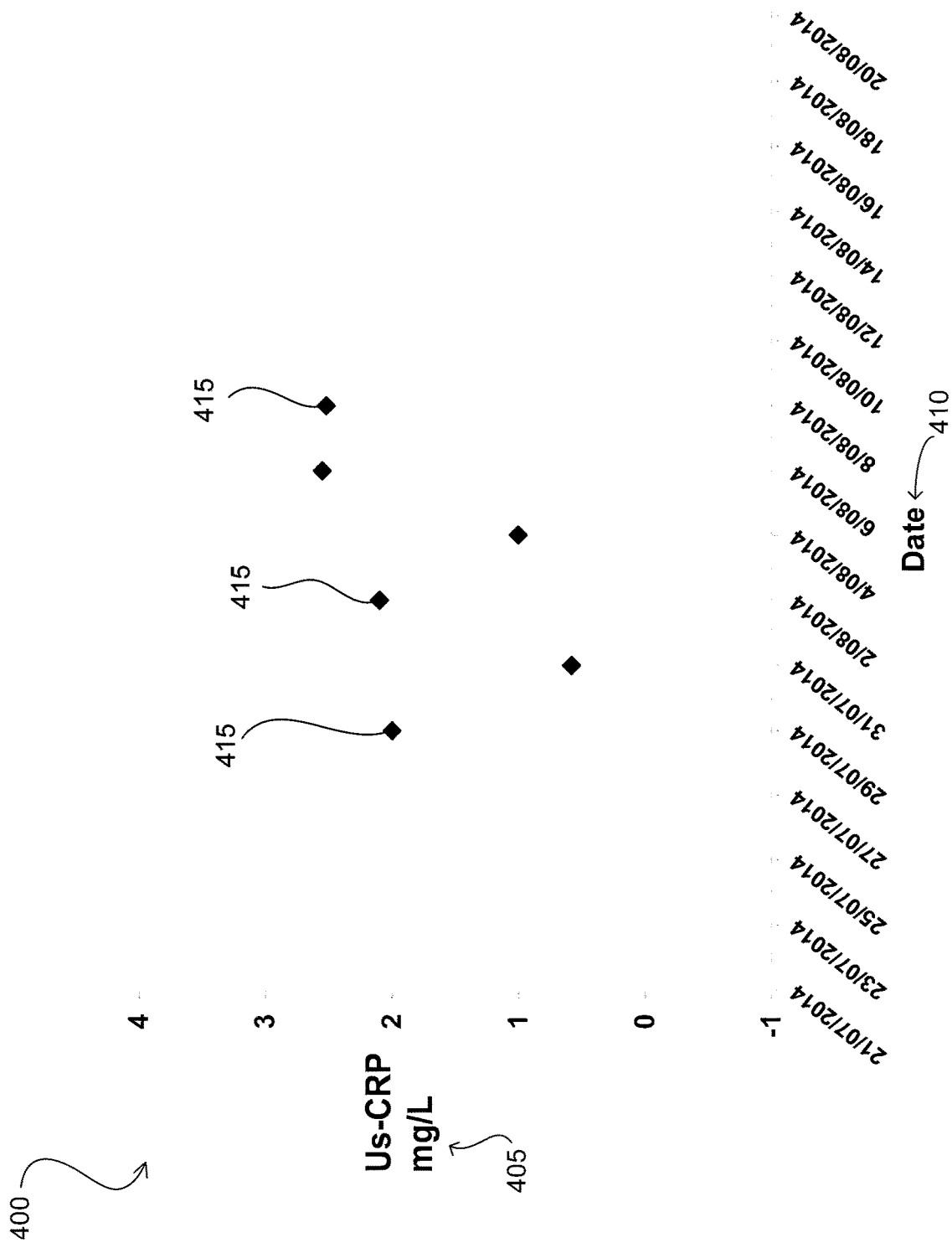

As shown in FIG. 4a, a graph 400 of Us-CRP mg/L 405 is plotted against date 410 over a period of 29 Jul. 2014 to 8 Aug. 2014. As shown in the graph 400 the immune system activity of the subject fluctuates. In this graph there is no interpretation of the data points 415 obtained from the subject. The data points 415 are as follows:

TABLE 1

| Date | Us-CRP |
|---|---|
| 29 July | 2 |
| 31 July | 0.58 |
| 2 August | 2.1 |
| 4 August | 1 |
| 6 August | 2.55 |
| 8 August | 2.52 |

The physiologic data is obtained and stored on the server 120 and in database 125.

As shown in FIG. 4b the graph 400 may be interpreted by the processing component in the server 120 to resolve the periodicity and dynamics of the immune cycle. By joining the data points 415 along line 420 while it is possible to interpret this good data using this arrangement it would be appreciated that unless continual data is obtained it is difficult to interpret the data unless periodic analysis is carried out.

Figure 4C:
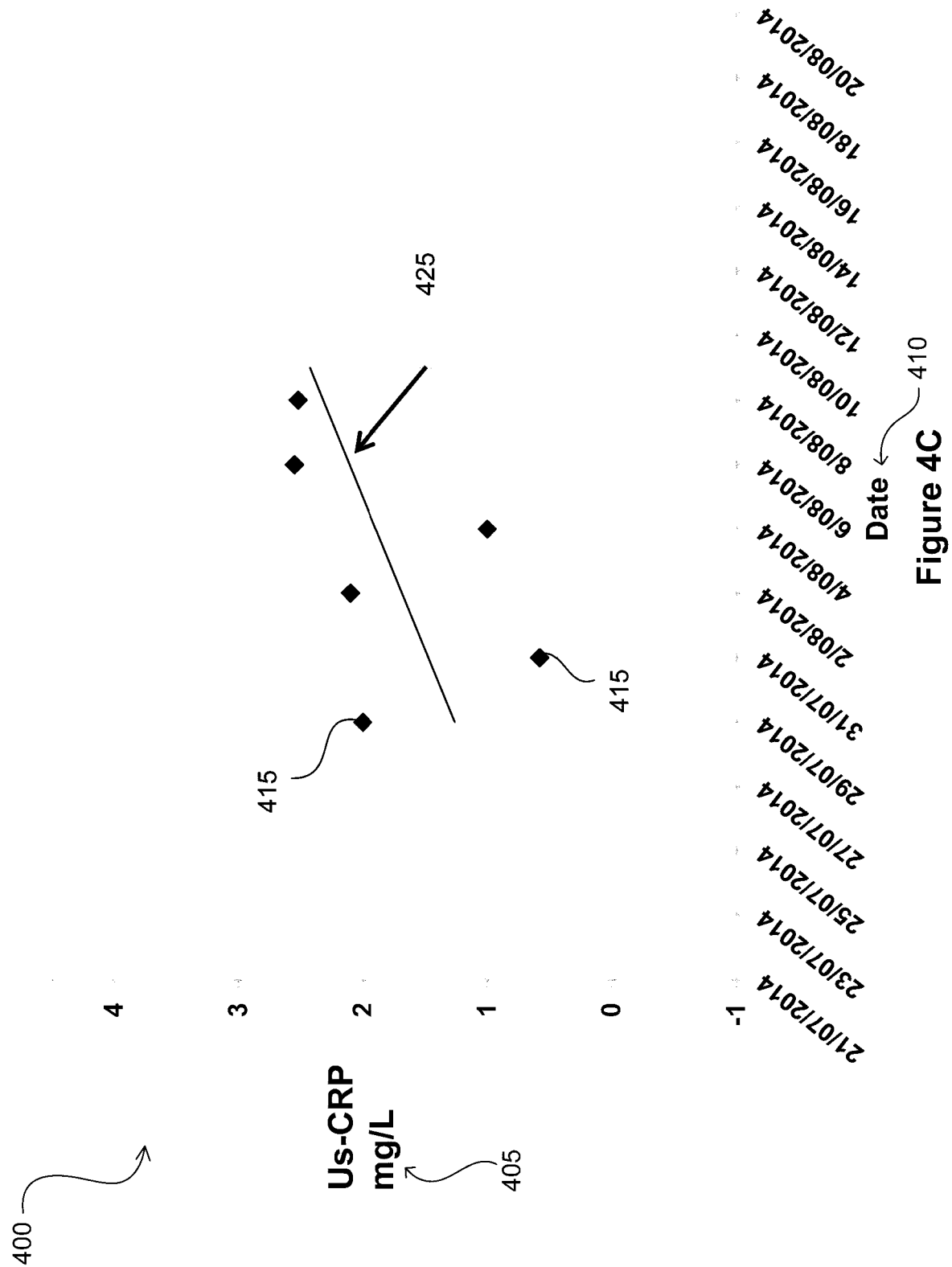

Similarly, in FIG. 4c the graph 400 includes points 415 in which linear trend analysis 425 is carried out but again suffers from not being able to identify the individual's immune cycle without appropriate context and analysis.

Figure 4D:
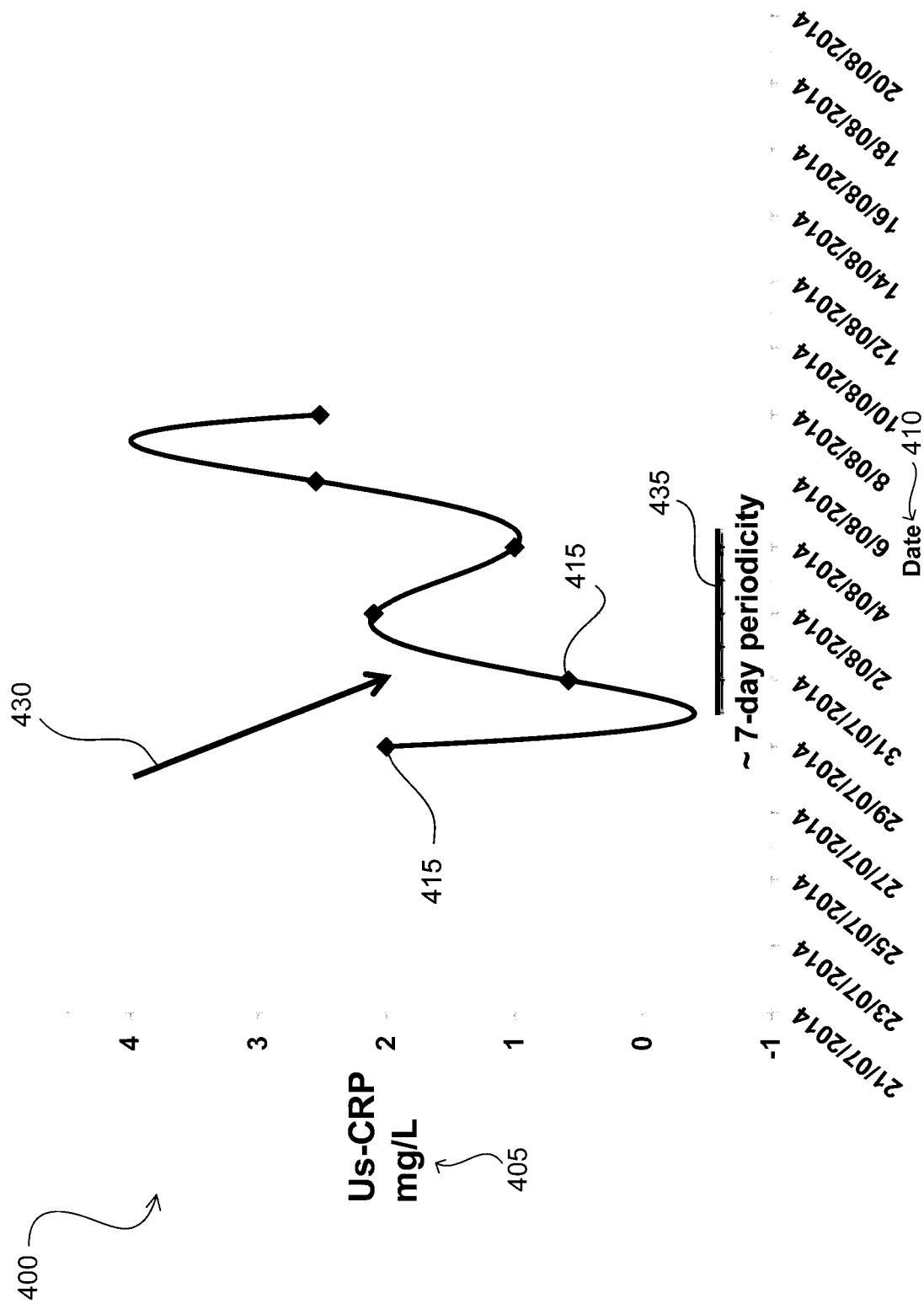

Preferably the system and method as previously mentioned uses a curve of best fit 430 to analyse the data as shown in the graph 400 in FIG. 4d. In which a period of approximately seven days 435 is discerned using curve of best fit, in this instance when a polynomial trend analysis (shown as curve 430) is applied to the data points 415.

The periodicity of the immune cycle can be derived from any other mathematical models as appropriate. In the present example it has been carried out by polynomial trend analysis (shown as curve 430). It will be appreciated that other analysis methods including but not limited to polynomial trend analysis, trigonometric analysis such as sign and cosine function, harmonic functions, periodic frequentation (or calculated manually by measuring the time period for one point in a wave of the cycle to the same point in the next wave, e.g. peak to peak or trough to trough or peak to trough for half a period and extending it). In short it will be appreciated that any number of mathematical models may be applied to determine a curve of best fit for the data and therefore highlight the periodicity of the subject's immune cycle.

Figure 4E:
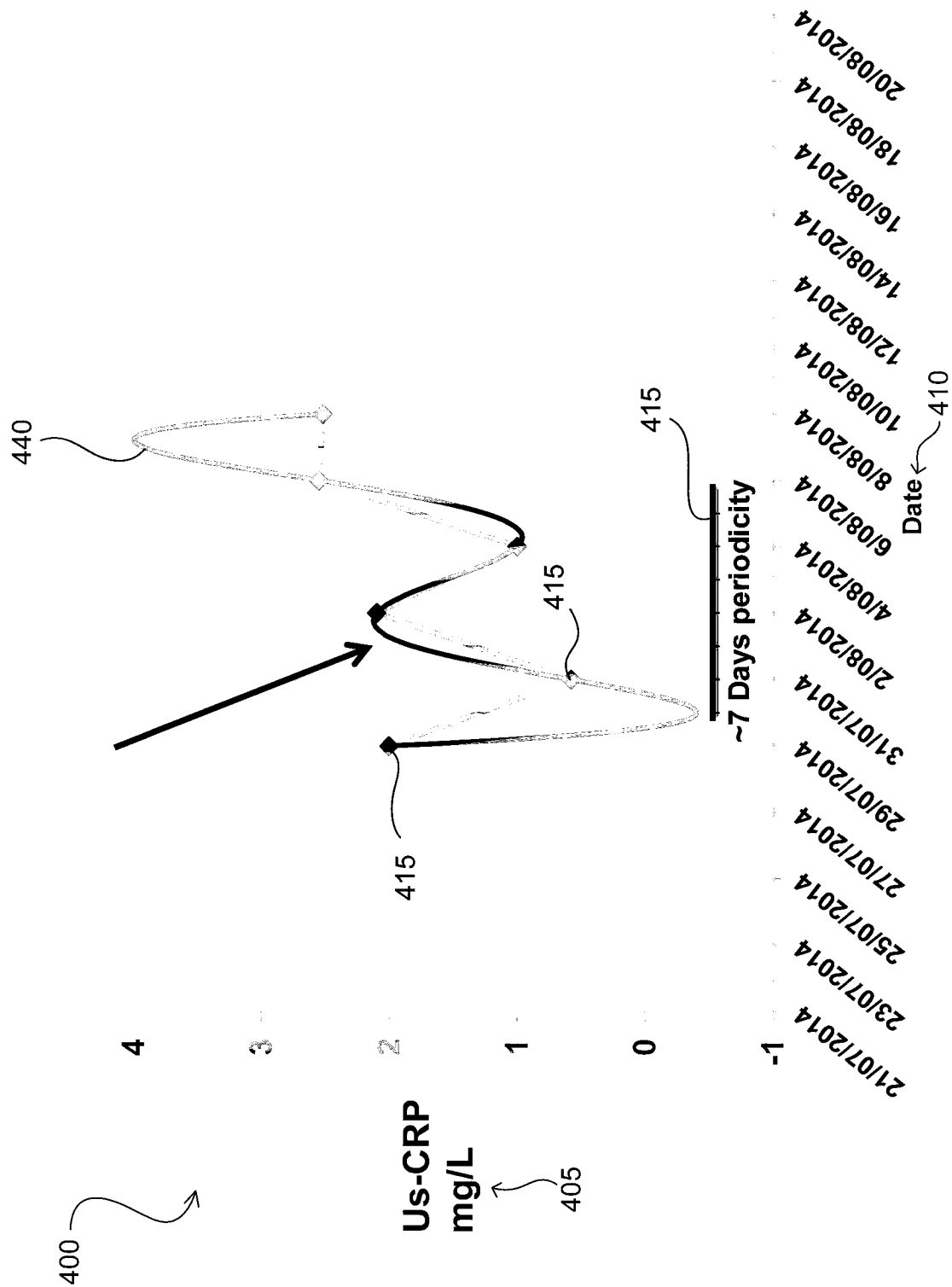

FIG. 4e is a graph 400 with a sine wave like function 440 applied with the same periodicity overlayed to enable extrapolation of the individual's predicted immune status and cycle in the future. As can be seen, the individual's immune cycle can be extrapolated from the data points 415 by the polynomial trend analysis 430 to determine at which point in the future the subject's immune status and cycle will be.

In FIG. 4e it can be seen that there are peaks and troughs in the immune activity over the time period and extrapolating those data points 415 provides an indication of the immune activity of the subject in the near future. At this point, the subject or a person using the system 100 may make a determination based on the particular day they are using the system as to whether or not the subject should engage in the "rest or stress" activities. For example, in the case of 2 Aug. 2014 to 4 Aug. 2014 the immune activity is decreasing, and the immune system is in an anti-inflammatory phase, therefore a decision may be made on these days to not carry out a certain activity, whereas on 6 Aug. 2014, in the pro-inflammatory phase it may be optimal to carry out certain activities.

FIGS. 4a to 4e are examples of blood readings, in particular Us-CRP in a subject as they relate to immune activity but it will be appreciated that other biomarkers can be used.

Figure 5A:
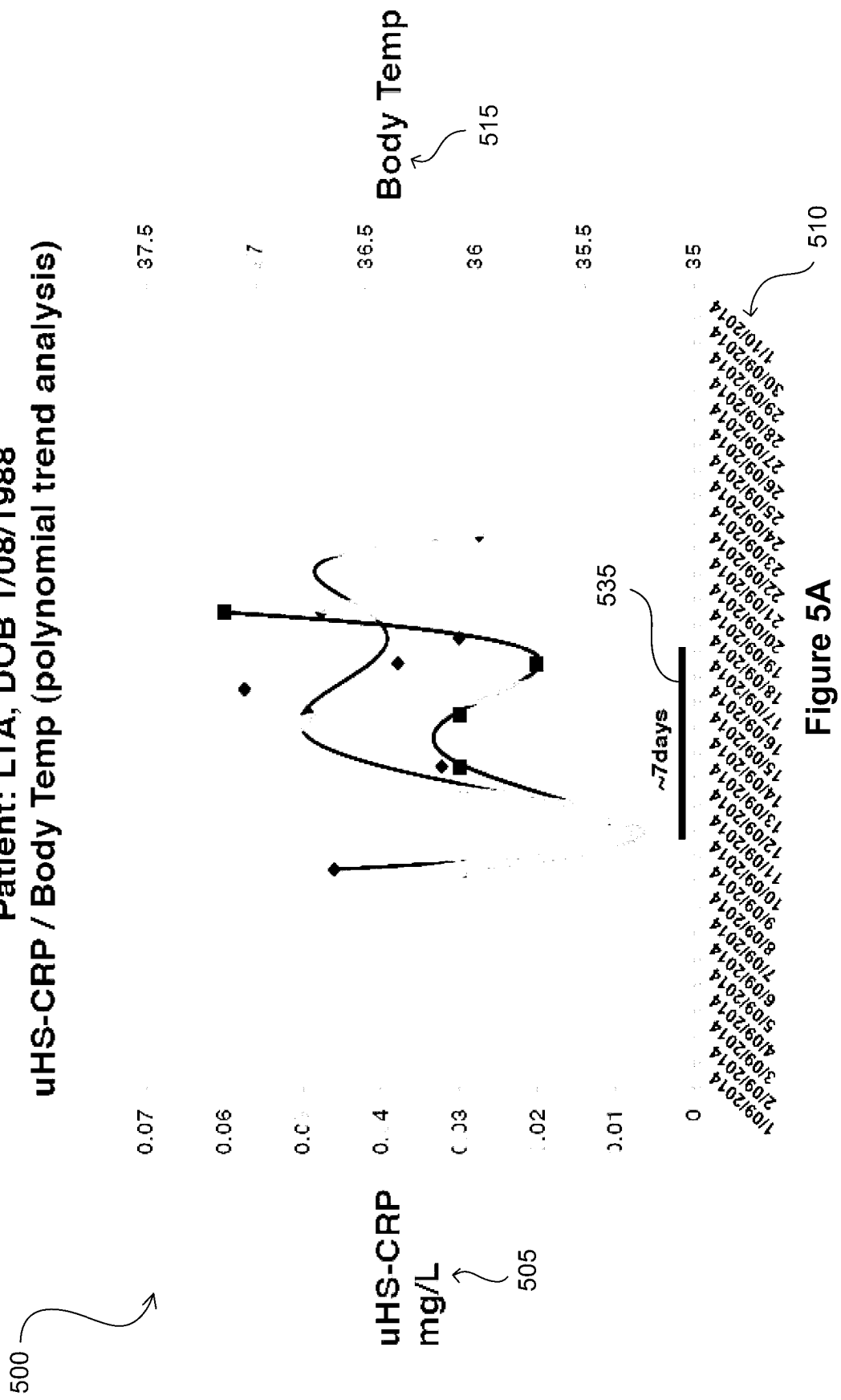

FIG. 5a shows a graph of Us-CRP 505 v time and body temperature (BT) 515 v time over the period of 1 Sep. 2014 to 1 Oct. 2014. As can be seen in the graph, both the body temperature and Us-CRP of the subject's cycle with a periodicity 535 of approximately 7-days when a best fit curve is applied to the data to resolve the periodicity and dynamics of the immune cycle. As can be seen, sufficient but not necessarily serial measurements are necessary to enable analysis using the curve of best fit periodicity model to determine the cycle. Below is a table of the dataset used in FIG. 5a:

TABLE 2

| Date | BT °C. expand | Us-CRP |
|---|---|---|
| 9 Sep. 2014 | 36.64 | 0.03 |
| 10 Sep. 2014 | | |
| 11 Sep. 2014 | | 0.01 |
| 12 Sep. 2014 | 36.05 | |
| 13 Sep. 2014 | 36.15 | 0.03 |
| 14 Sep. 2014 | | |
| 15 Sep. 2014 | 36.75 | 0.03 |
| 16 Sep. 2014 | 37.05 | |
| 17 Sep. 2014 | 36.35 | 0.02 |
| 18 Sep. 2014 | 36.07 | |
| 19 Sep. 2014 | 36.7 | 0.06 |
| 20 Sep. 2014 | | |
| 21 Sep. 2014 | | |
| 22 Sep. 2014 | 35.95 | |

In operation, a sampling component 130 is be worn by a subject. The sampling component 130 is a device which constantly monitors temperature and sends it to the server 120. The graph of the immune cycle provided in FIG. 5a is a result of the data obtained by the sampling component 130. The sampling component 130 may be a thermometer or a device similar to the Duofertility™ device and the like (i.e. a device which takes numerous temperature readings throughout the day/night to ascertain the true basal temperature of a subject). The system 100 of the present invention utilises this data in the processing component to analyse this physiological data and thereby determine the periodicity and dynamics of the immune cycle of the subject.

Figure 5B:
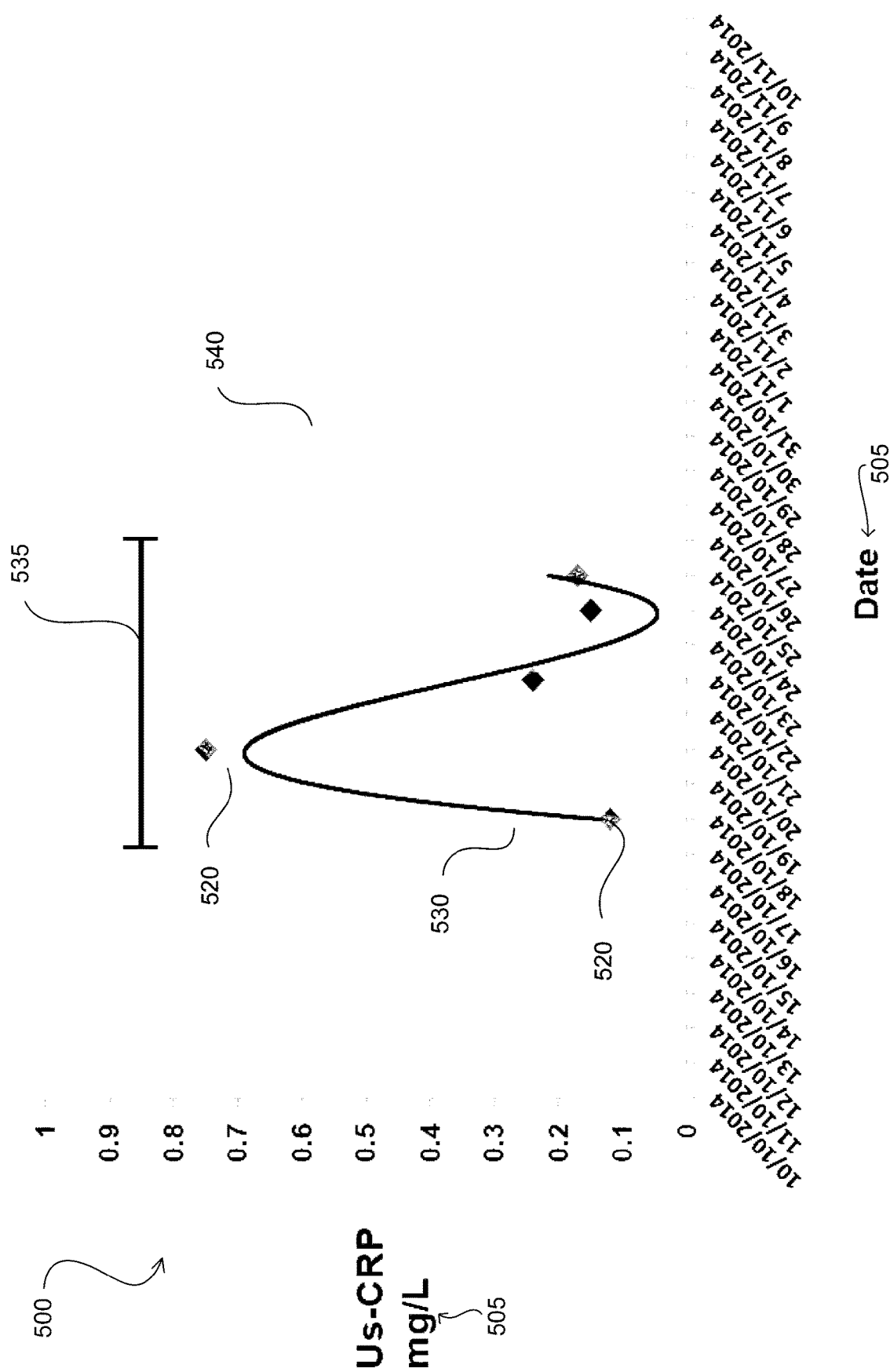

FIG. 5b shows a graph of Us-CRP mg/L 505 versus time/date 505 of a subject who is female who is 24 years of age, is a non-smoker, attends the gym five days per week on average and is otherwise a fit and healthy person (but not a professional athlete).

As can be seen in the graph 500 the Us-CRP 505 of the subject cycles over a period 535 of approximately seven days as shown by polynomial trend analysis 530 of data points 520. The data for the table is shown in Table 3 below:

TABLE 3

| Date | Us-CRP |
|---|---|
| Oct. 18, 2014 | 0.12 |
| Oct. 20, 2014 | 0.75 |
| Oct. 22, 2014 | 0.24 |
| Oct. 24, 2014 | 0.15 |
| Oct. 25, 2014 | 0.17 |

FIG. 5c is a graph 500 of Us-CRP 505 versus date 510 of the subject who is a 28 year old male who is a smoker and a non-gym goer. Again, over a period 535 of seven days it can be seen from data points 520 having polynomial analysis 530 applied there is a periodicity of the immune cycle as shown against sine wave like function 540.

The data for FIG. 5c is shown below:

TABLE 4

| Date | Us-CRP |
|---|---|
| Oct. 20, 2014 | 0.26 |
| Oct. 22, 2014 | 0.18 |
| Oct. 24, 2014 | 0.23 |
| Oct. 25, 2014 | 0.54 |

Figure 5D:
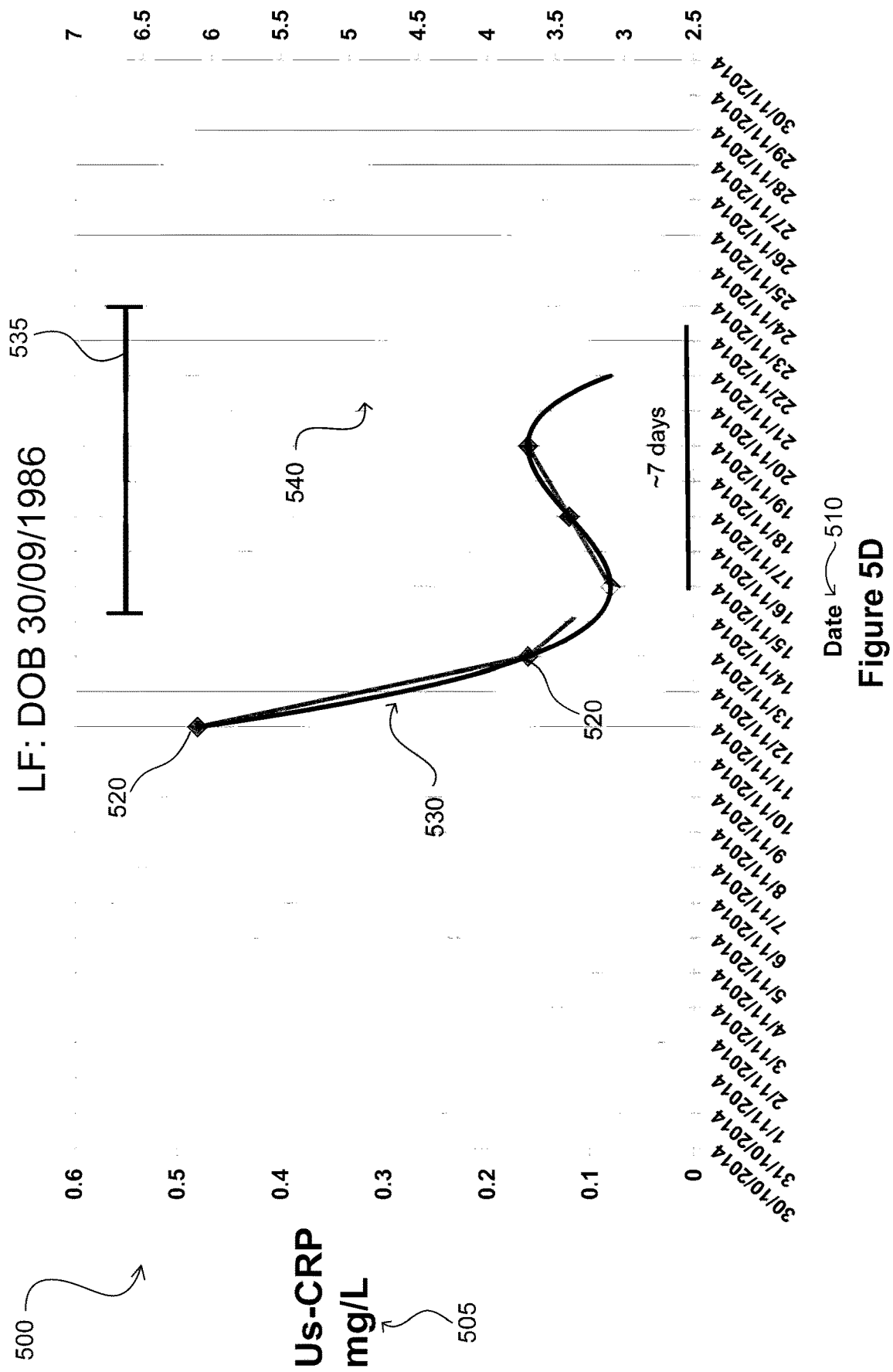

FIG. 5d is a graph 500 of Us-CRP 505 versus date 510 of the subject who is a male, 28 years of age, a non-smoker and frequents the gym approximately 3 times per week. Again, over a period 535 of seven days it can be seen from data points 520 having polynomial analysis 530 applied there is a periodicity of the immune cycle as shown against sine wave like function 540.

The data for FIG. 5d is shown below:

TABLE 5

| Date | Us-CRP |
|---|---|
| Nov. 11, 2014 | 0.48 |
| Nov. 13, 2014 | 0.16 |
| Nov. 15, 2014 | 0.08 |
| Nov. 17, 2014 | 0.12 |
| Nov. 19, 2014 | 0.16 |

Figure 5E:
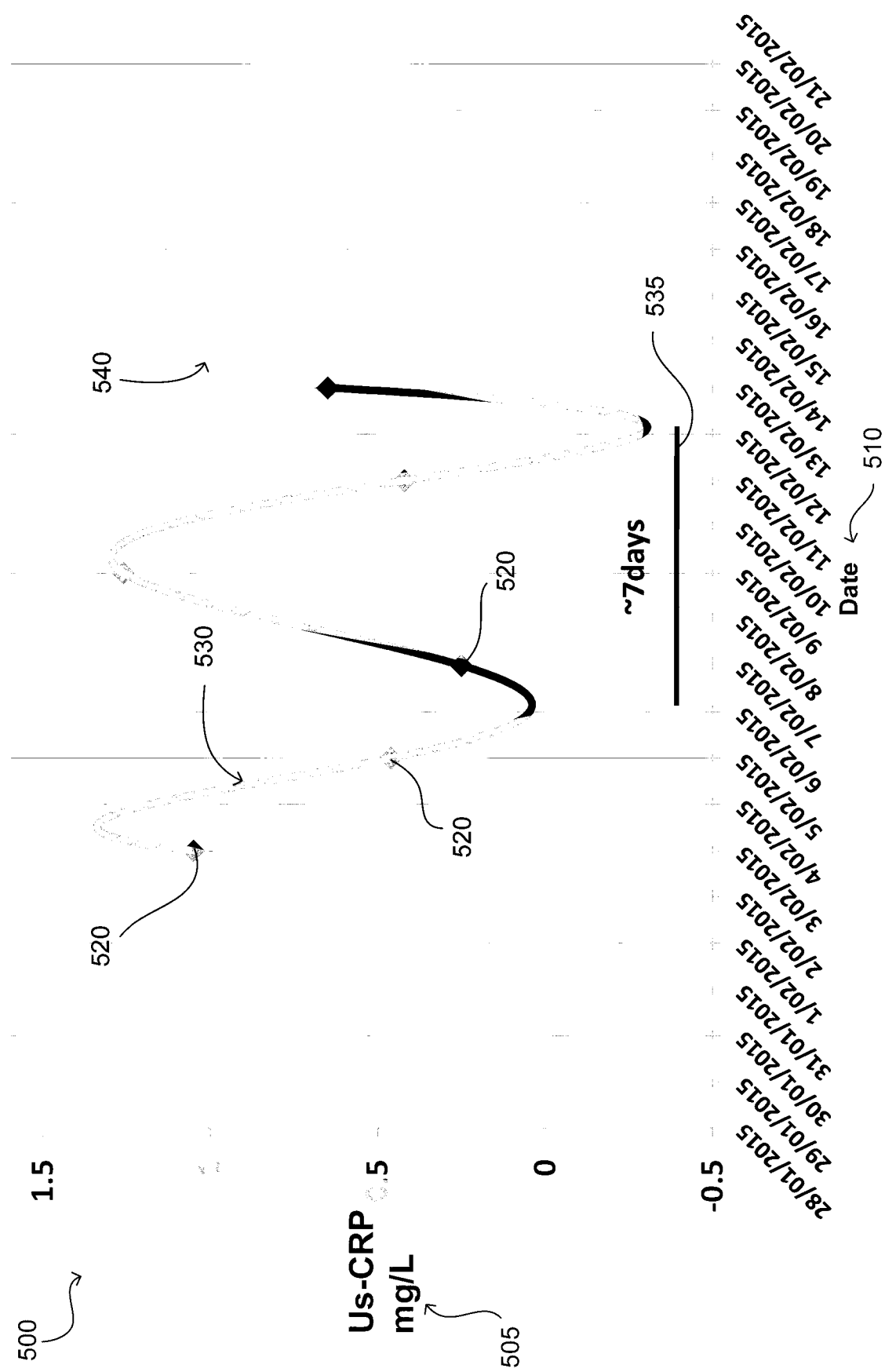

FIG. 5e is a further graph 500 of Us-CRP 505 versus date 510 of a subject who is a male, 28 years of age, a smoker and an irregular gym goer. Again, over a period 535 of seven days it can be seen from data points 520 having polynomial analysis 530 applied there is a periodicity of the immune cycle as shown against sine wave like function 540.

The data for FIG. 5e is shown below:

TABLE 6

| Date | Us-CRP |
| --- | --- |
| Feb. 3, 2015 | 1.05 |
| Feb. 5, 2015 | 0.46 |
| Feb. 7, 2015 | 0.25 |
| Feb. 9, 2015 | 1.26 |
| Feb. 11, 2015 | 0.42 |
| Feb. 13, 2014 | 0.65 |

Figure 5F:
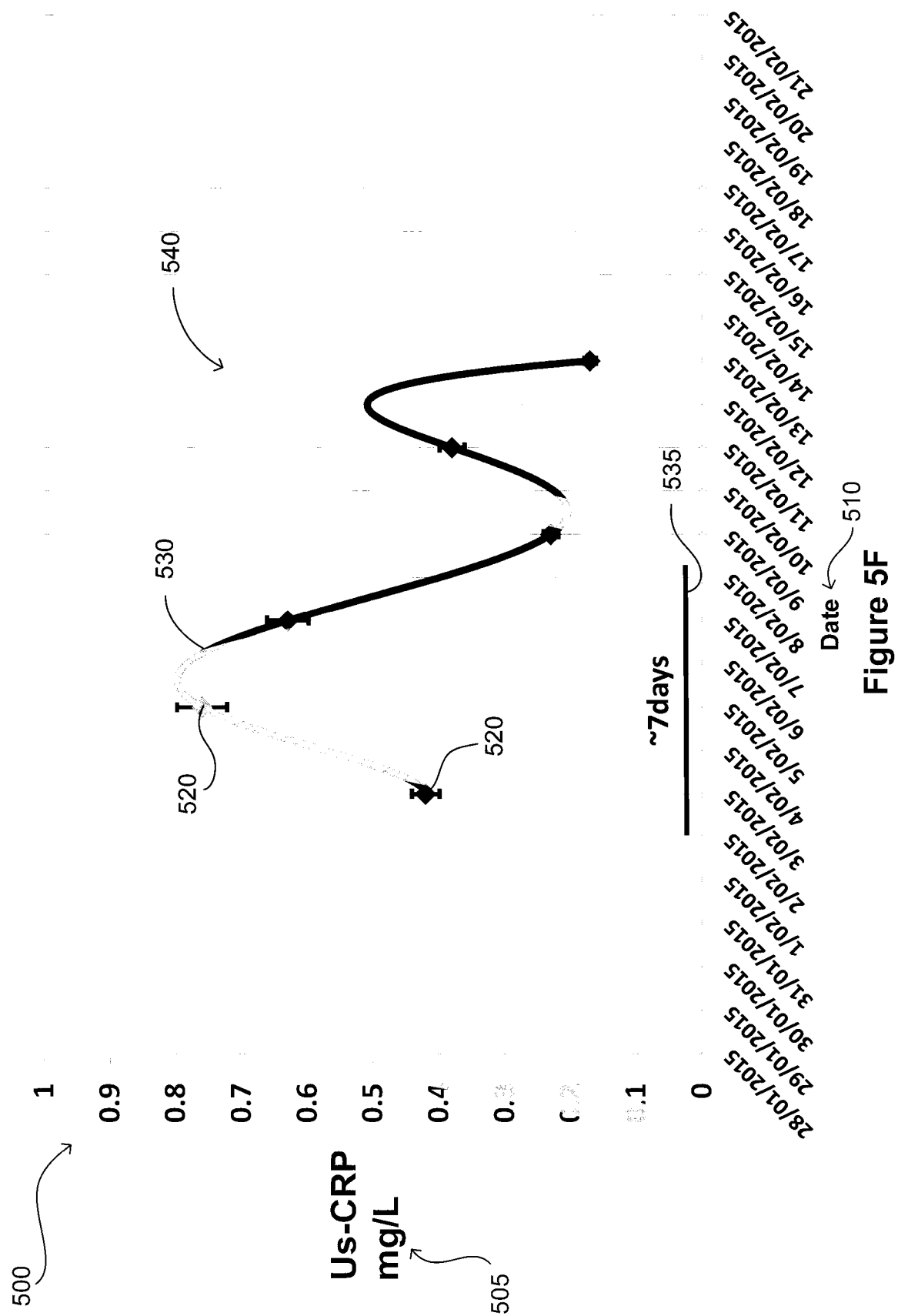

FIG. 5f is a further graph 500 of Us-CRP 505 versus date 510 of a subject who is a male, 28 years of age, a non-smoker and an irregular gym goer. Again, over a period 535 of seven days it can be seen from data points 520 having polynomial analysis 530 applied there is a periodicity of the immune cycle as shown against sine wave like function 540.

The data for FIG. 5f is shown below:

TABLE 7

| Date | Us-CRP |
| --- | --- |
| Feb. 3, 2015 | 0.42 |
| Feb. 5, 2015 | 0.76 |
| Feb. 7, 2015 | 0.63 |
| Feb. 9, 2015 | 0.23 |
| Feb. 11, 2015 | 0.38 |
| Feb. 13, 2014 | 0.17 |

Figure 5G:
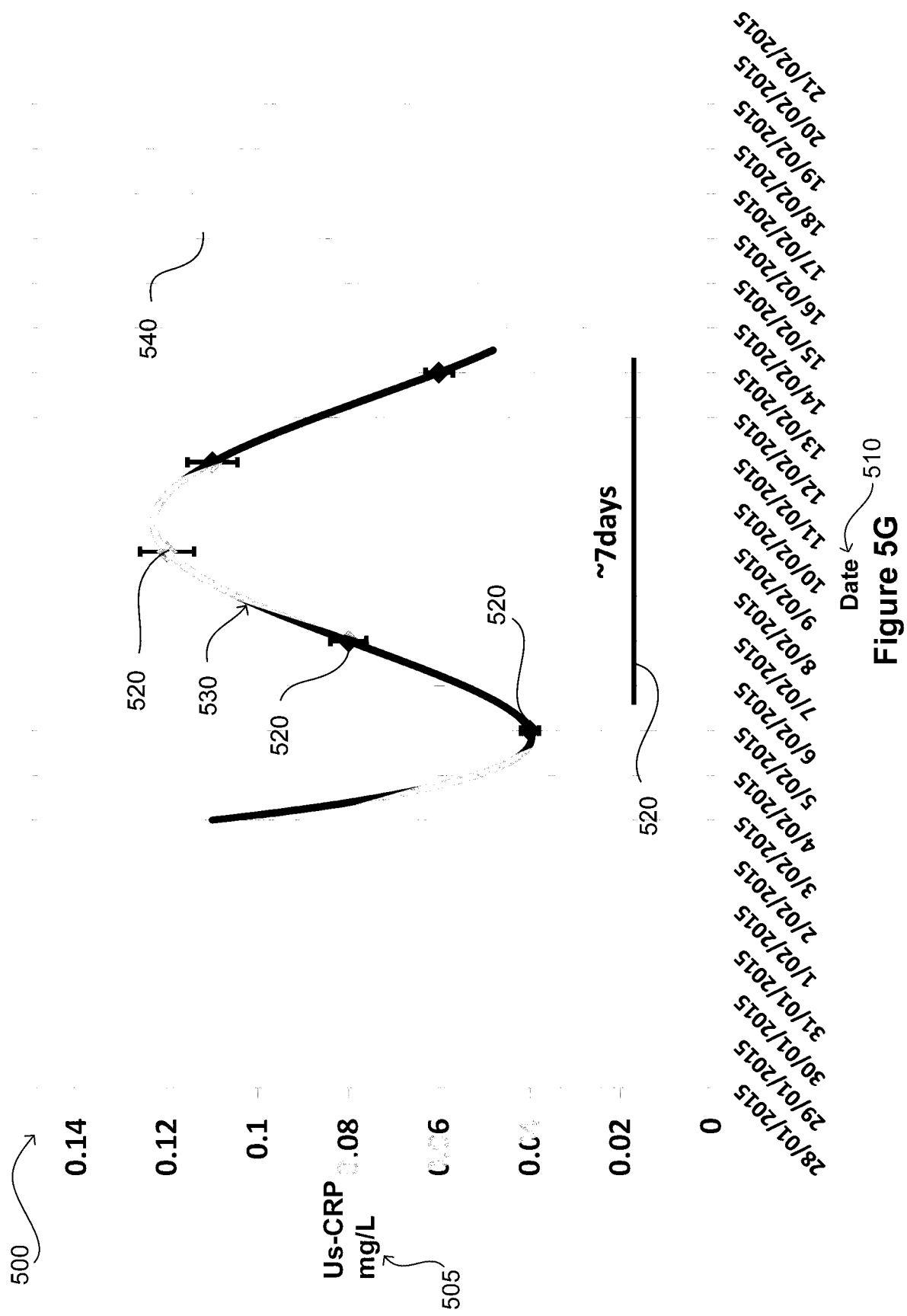

FIG. 5g is a further graph 500 of Us-CRP 505 versus date 510 of a subject who is a male, 28 years of age, a smoker and a regular gym goer. Again, over a period 535 of seven days it can be seen from data points 520 having polynomial analysis 530 applied there is a periodicity of the immune cycle as shown against sine wave like function 540.

The data for FIG. 5g is shown below:

TABLE 8

| Date | Us-CRP |
| --- | --- |
| Feb. 5, 2015 | 0.04 |
| Feb. 7, 2015 | 0.08 |
| Feb. 9, 2015 | 0.12 |
| Feb. 11, 2015 | 0.11 |
| Feb. 13, 2014 | 0.06 |

It can be seen that the range of the measurements of the biomarker used (Us-CRP) vary between individuals but are all within an acceptable "normal" range for the assay. The accuracy of the measurements is dependent on the choice of the marker and the sensitivity of the device and or assay used to determine the measurements. Without being limited by theory, these variations in ranges could be due to genetic or environmental factors. Regardless of the variability in the ranges of the biomarker between individuals, the immune status and or immune cycle is discernable in all individuals tested.

Figure 6:
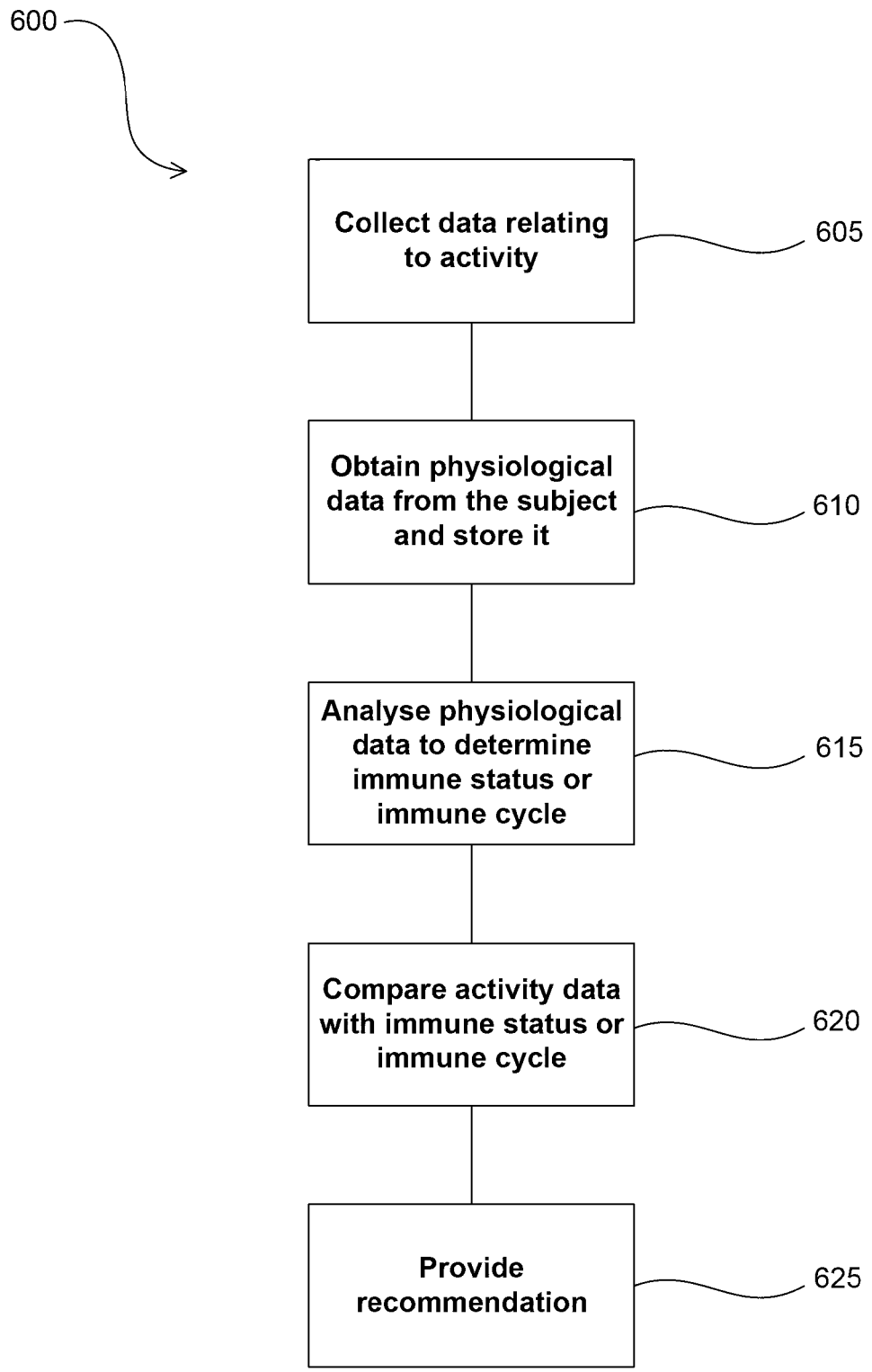
FIG. 6 a flow diagram illustrating an example method of the invention according to another embodiment.

FIG. 6 illustrates an alternative embodiment of the present invention, namely a method 600 for improving a subject's physiological response to an activity and providing a recommendation. At step 605 data is obtained via electronic devices 105 or 110. The data obtained relates to the activity that the subject is participating in. For example, the activity may be training, rehabilitation, elective or non-urgent surgery, general well-being or a health action plan. This may be selected from a menu or similar or may be entered manually. The data relating to the activity may be obtained manually from the user input component of the system or may be predetermined for a particular activity. For example, the system may be a pre-surgery or training system in which case the activity data may be predetermined. In any event, some data may additionally be input relating to the activity such as, for example, the type and or intensity or volume of exercise being carried out. The data at step 605 may be obtained via an electronic input device such as a keyboard via electronic devices 105, 110. In particular, the data obtained may relate to the activity (e.g., health regimen, elective non-urgent surgery, rehabilitation) that the subject is participating in. For example, data that may be obtained via devices 105 and 110 may include the type of activity that is being carried out, for example, training, rehabilitation, a particular sport, the type of mammal that the activity relates to (e.g., a human, a horse or a dog). Anthropometric or biometric data may be obtained as well which may include the subject's age, weight, height, ethnic background and in addition other information such as nutritional and dietary intake, lifestyle habits. Control then moves to step 610 in which a sampling component 130 obtains physiological data from the subject and stores it on a database 125 via server 120. The physiological data may include a biomarker, or immune system marker, biometric data or physiological data such as, the basal or resting temperature of the subject for example. These may be obtained via various sampling devices, or, in the case or temperature for example, the temperature may be input manually by the subject. Blood test results such as CRP may also be manually input by a doctor or coach or trainer. For example, obtaining physiological data automatically via a sampling device may be via a wearable device worn by the subject. Obtaining physiological data manually via the sampling device may be the user manually entering values (such as temperature etc.).

Once the physiological data has been obtained, at step 615 a processing component within the server 120 analyses the physiological data to determine and resolve the periodicity and dynamics of the immune cycle or immune status. In particular, the server 120 then analyses the physiological data to estimate the immune status and or immune cycle. The server 120 then sends the information relating to the immune status and or cycle to the electronic device 105, 110 via the network 115.

After determining the immune status and or cycle of the subject (and in particular where in the immune cycle the subject is currently (immune status), at step 620 the activity data obtained at step 605 is compared against the immune status and or immune cycle of the subject using an inference engine to derive a conclusion from the facts and rules contained in a knowledge database. The present invention uses the results of the analysis of the data to derive the immune status or cycle of the subject to create a recommendation related to an activity so as to determine the optimal time for carrying out a particular activity or schedule of activity in the near future. Alternatively, the recommendation may provide a list of activities related to the current status.

Control then moves to step 625 in which a recommendation is provided via devices 105, 110.

Figure 7:
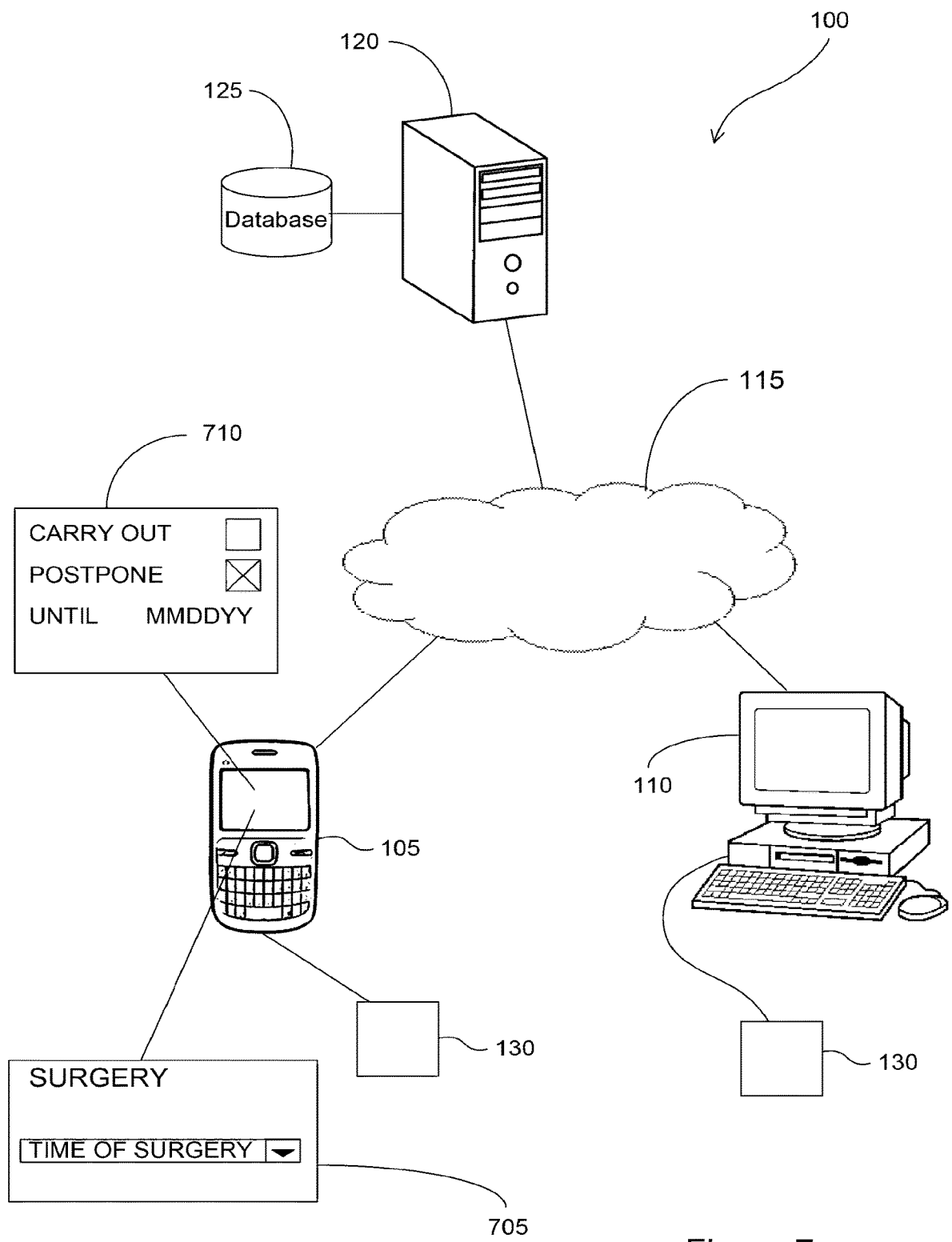
FIG. 7 is a schematic diagram illustrating use of the system and method of the present invention prior to a surgical procedure.

FIG. 7 schematic diagram of the invention as it relates to the activity of carrying out surgery on a subject. In operation, the subject may be planning or scheduled to undergo elective or non-urgent surgery and so as to ensure that the surgery is carried out at an optimal time to enhance recovery or ascertain the severity of the impact of the surgery in light of the subject's immune cycle or immune status, the system 100 of the present invention is utilised. One or more sampling components 130 are used in association with device 105, 110 to measure and obtain physiological data of the subject. As described with reference to FIG. 1, the physiological data is communicated via a communications network 115 to server 120. In the context of elective or non-urgent surgery the sampling components 130 may include blood analysis devices, saliva sampling devices and the like. They may be portable, or, since surgeries are likely to occur in a hospital, they may be standalone non-portable equipment. The system 100, via the electronic device 105, 110 provides an input screen 705 for the user of the system to provide information relating to the activity. In the context of surgery, screen shot 705 may include any number of parameters which will assist the system 100 in determining whether or not it is an appropriate time or to enhance recovery or ascertain the severity of the impact of the surgery in light of the subject's immune cycle and status for time of the surgery to be carried out on the subject. For example, if the proposed date or time of the surgery is known it is inserted. The proposed time of the surgery may be based on conditions such as the availability of the surgeon and may have one or more time windows or options available for surgery. Alternatively, if a number of potential dates are available for selection these can be inputted and a recommendation can be made based upon those inputted The system 100 utilises this activity data together with the physiological data and the subject's immune cycle and status to determine an appropriate recommendation. At the server 120 the physiological data is retrieved from the database where it is stored and analysed to estimate a periodicity of the cycling of the physiological data and thereby determine the current or near future status of the immune cycle of the subject. By comparing the immune cycle with the information related to the activity gathered via display 705 on devices 105, 110, the system 100 uses an inference engine located on server 120 to determine when an appropriate time for surgery to be carried out on a subject is so as to enhance recovery or ascertain the severity of the impact of the surgery in light of the subject's immune cycle. For example, if the subject is in a pro-inflammatory phase in their immune cycle and according to the information received via screen shot 705 surgery is to be carried out immediately then the system 100 will determine that in this instance that the surgery would not be optimal or should not be carried out and this may be displayed on screen 710 on device 105 or 110. In another aspect, the system 100 will determine the impact in this instance of the surgery and recommend actions such as taking anti-inflammatory medication to reduce the heightening of the inflammatory response such as swelling and soreness and this may be displayed on screen 710 on device 105 or 110.

Figure 8:
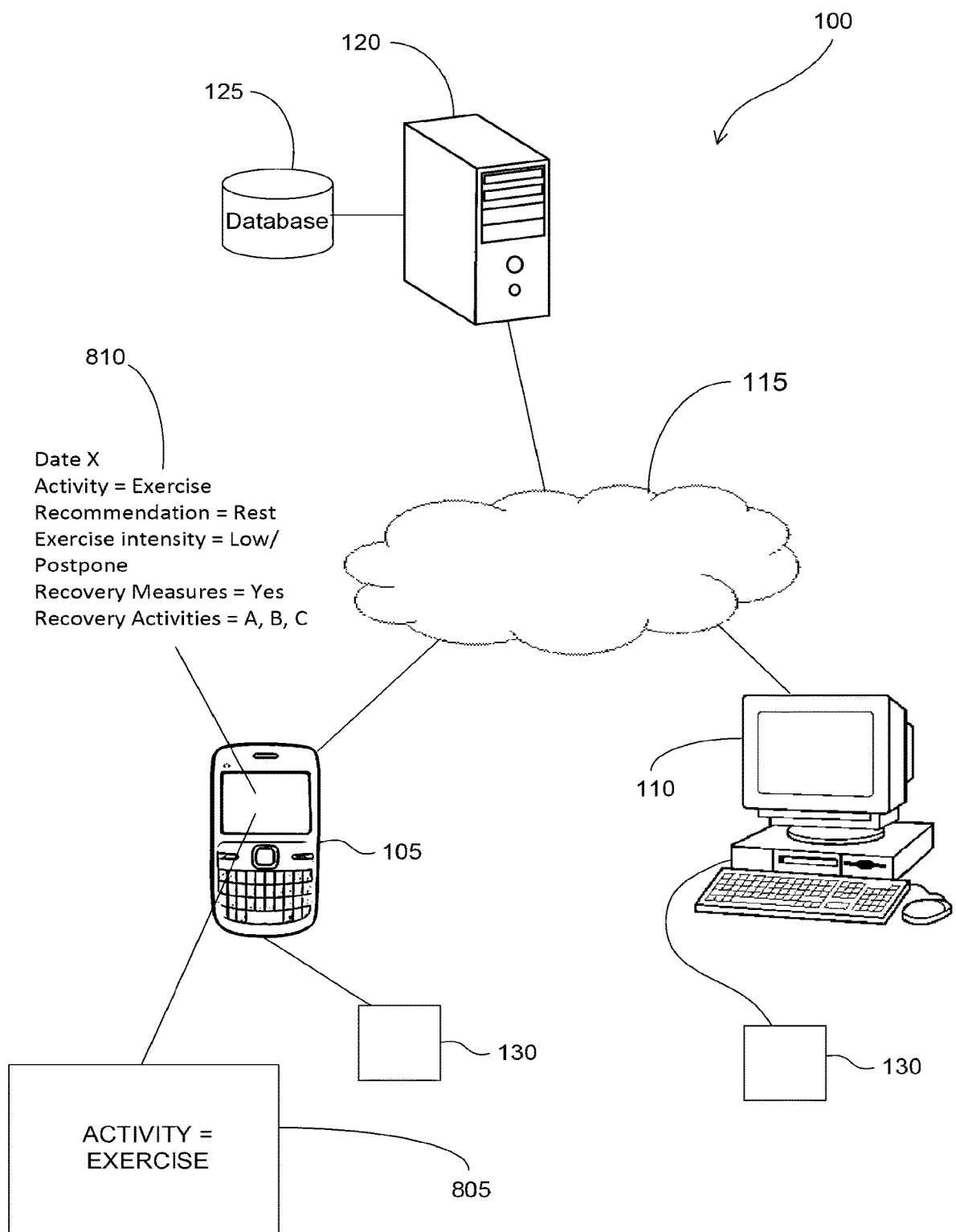
FIG. 8 schematic diagram illustrating use of the system and method of the present invention as part of an action plan related to lifestyle.

FIG. 8 schematic diagram of the invention as it relates to the activity of a lifestyle choice in a subject where the advice may be to "rest" or to "stress", where rest may indicate an early night, no or less intense physical activity or training and "stress' may indicate suitable time for more intense activity because at this time there will be less severe consequences, minimised recovery time from the same or more intense activity. In operation, the subject may be planning or scheduled to socialise and so as to determine whether or not to "rest or stress" (based on the subject's immune status or cycle) the system 100 of the present invention is utilised. One or more sampling components 130 are used in association with device 105, 110 to measure and obtain physiological data of the subject. As described with reference to FIG. 1, the physiological data is communicated via a communications network 115 to server 120. In the context of a lifestyle choice the sampling components 130 may include temperature or saliva sampling devices and the like.

The system 100, via the electronic device 105, 110 provides an input screen 805 for the user of the system to provide information relating to the activity. In the context of a lifestyle choice, screen shot 805 may include any number of parameters which will assist the system 100 in determining whether or not it is an appropriate time to undertake an activity. For example, whether or not the subject should exercise or the intensity of the work out. In this case, the activity is exercise and the system and method of the invention will determine a recommendation. Other information may be obtained such as the type or intensity of activity and the proposed time for the activity may be obtained.

The system 100 utilises this activity data together with the physiological data and the subject's immune cycle and status to determine an appropriate recommendation. At the server 120 the physiological data is retrieved from the database where it is stored and analysed to estimate a periodicity of the cycling of the physiological data and thereby determine the immune cycle and status of the subject. By comparing the immune cycle and status with the information related to the activity gathered via display 805 on devices 105, 110, the system 100 uses an inference engine located on server 120 to determine whether or not it is an appropriate time or the consequences for the subject if they undertake a particular activity. For example, if the subject is in a pro-inflammatory phase in their immune cycle and, according to the information received via screen shot 805, the activity is an inflammatory stimulating activity such as physical training, then the system 100 will determine that in this instance that the subject should "rest" or undertake lighter or less intense activity or recommend recovery measures such as taking anti-inflammatory medication, ice baths or such to reduce the heightening of the inflammatory response such as swelling and soreness likely to result from the activity. This may be displayed on screen 810 on device 105 or 110. In this example, 810 outputs the date, the type of activity, a recommendation based on the immune cycle or status of the subject. In addition, it may display or output specific parameters such as the recommended intensity of exercise given the immune cycle and status, whether recovery measures should be in place, and suggested recovery activities for example. If the activity is one such as vaccination where it is used to stimulate an immune response, and the response desired from the activity is a heightened immune response, then the system will send a different recommendation such as best dates according to the current or near future status of the individual's immune cycle.

While the examples of FIGS. 7 and 8 relate to activities of elective or non-urgent surgery and lifestyle choices respectively, it will be appreciated that the system and method of the present invention allows for the provision of recommendations on an activity for the benefit of the subject and to minimise the risk of injury and prolonged recovery in the subject. In particular, the present invention provides coaches as well as athletes the ability to assess the influence of the immune system on the athletic potential of a subject(s) as well as to structure a team as a consequence thereby enabling them to produce the most effective and/or the most ideal team. Coaching decisions may then be based on where a subject is in their immune cycle on a given day or future date. For example, current training regimens are unable to determine whether a subject is likely to respond optimally to training, performance, recovery and injury. Knowledge of an individual's immune status will help manage training, performance, potential injury and recovery. The system and method of the present invention assist in selection of a player for example in light of their immune status.

Advantageously, the system and method of the present invention allows for the provision of recommendations where the activity is rehabilitation so as to minimise/hasten recovery time, prevent overtraining, prevent the compounding of existing injuries and the chance of further injury(s), rest and recover at the appropriate time as well as increase the efficiency of training and rehabilitation.

In addition, the system and method of the present invention may assist in recognising to whom and when a possibly small but critical difference in a subject's training and or playing schedule should be made. For example, via the system and method of the invention, selecting appropriate times to train, type of training or rest and recover based on the individual's immune status and likely effects in recovery times in a subject after training and/or injuries.

Using the processed biometric and physiological data and recommendations from the system and method of the invention, various individual or coaching decisions affecting physical outcomes may be made. For example, a coach may decide to select an athlete to play ("play an athlete") or decide not to select an athlete to play or reduce playing time "bench an athlete" depending on the athlete's immune status, indicating an ability or inability to perform, respond or recover at the required or ideal level. Alternatively, a coach may review the information provided and/or recommendations provided from the system and make a coaching decision based on the recommendation. This coaching step would be implemented prior to or during a sporting event. For example, based on the provided physiological data, the coach may determine that a particular athlete is not capable of playing to full potential/wants to avoid over doing it, exposing the athlete to injury (because recovery time may be long if an injury is sustained) or overstressing the player. The coach may then decide to rest the athlete or temporarily remove the athlete from the sporting event until he or she is rested and ready to return to the game or not return at all so as to minimise any detrimental consequences. Further, the coach may decide to rotate players during an event to ensure athletes are performing optimally for the entirety of the event and/or not at heightened risk and detrimental immunological consequences from injuries.

The system and method of the present invention allows for the provision of recommendations where the activity is vaccination so as so maximise the response to the vaccine.

The system and method of the present invention further can be applied to subjects who have suffered physical injuries or insults including but not limited to those of a serious nature such as those that have resulted from a traumatic event such as a heart attack or stroke or motor vehicle accident, spinal cord injury, loss of limb(s) and brain damage who often undergo rehabilitation, physiotherapy and training as well as those of a non-serious nature including but not limited to bone fractures, muscle tears, pulls and strains and torn ligaments who also often undergo rehabilitation, physiotherapy and training. These subjects will benefit from a training or rehabilitation action plan that takes into consideration their immune cycle and status so as to minimise or hasten recovery time, prevent overtraining, prevent the compounding of existing injuries and the chance of further injury(s) as well as increase the efficiency of training and rehabilitation. There is known variability in soreness and recovery in individuals who may undertake the same activity. Knowledge of immune status of the individual will provide insights into the response to the activity. For example, if the individual is in a pro-inflammatory state this may lead to an amplified immune response and or a longer recovery time. Recommendations for recovery measures would be given. Alternatively if an individual is in an anti-inflammatory phase, recovery time and soreness would be shorter.

The above description of embodiments of the present invention is provided for purposes of description to one of ordinary skill in the art. It is not intended to be exhaustive nor to limit the invention to a single disclosed embodiment. It should be appreciated that various changes and modifications may be made to the embodiments described herein without departing from the spirit or scope of the invention. Accordingly, this invention is intended to embrace all alternatives, modifications and variations of the present invention that have been discussed herein, and other embodiments that fall within the spirit and scope of the above described invention.

The invention claimed is:

1. A method for administering a preventative vaccine to a healthy or non-chronically diseased subject, comprising:
   a) receiving, by at least one processor, three or more measurements of a physiological data parameter of the healthy or non-chronically diseased subject taken over a period of time sufficient to resolve the periodicity of the subject's immune cycle, wherein the physiological data parameter is selected from at least one of an immune system marker and body temperature data of the subject;
   b) determining, by the at least one processor and based on serial time dependent variations in the three or more measurements of the physiological data parameter, the periodicity of the subject's immune cycle to thereby determine a future point in time when the subject will be in a pro-inflammatory phase; wherein the periodicity of the immune cycle is a non-diurnal periodicity which is greater than 1 day; and
   c) administering a preventative vaccine to the subject at the point in time when the subject will be in a pro-inflammatory phase.

2. The method of claim 1, wherein the periodicity of the immune cycle is 3 to 15 days and the future point in time when the subject will be in a pro-inflammatory phase is within the next 15 days.

3. The method of claim 1, wherein the future point in time when the subject will be in a pro-inflammatory phase is within the next 10 days.

4. The method of claim 1, wherein the future point in time when the subject will be in a pro-inflammatory phase is within the next 7 days.

5. The method of claim 1, wherein the three or more measurements of the physiological data parameter are gathered from a sensor.

6. The method of claim 5, wherein the sensor includes one or more devices which measure physiological data.

7. The method of claim 5, wherein the sensor includes at least one of a contact or non-contact temperature sensor, a blood biomarker sensor, a blood testing unit and a salivary collection unit.

8. The method of claim 1, wherein step a) comprises receiving three or more measurements of a second physiological data parameter taken over a period of time sufficient to resolve the periodicity of the subject's immune cycle, wherein the second physiological data parameter is selected from at least one of an immune system marker, and body temperature data of the subject and wherein the periodicity of the subject's immune cycle is determined based on serial time dependent variations in the first and second physiological data parameters.

9. The method of claim 1, wherein determining the periodicity of the subject's immune cycle comprises determining a curve which fits the three or more measurements.

10. The method of claim 1, wherein determining the periodicity of the subject's immune cycle comprises one or more of: polynomial trend analysis, trigonometric analysis, harmonic function analysis and periodic frequentation analysis.

11. The method of claim 1, wherein the physiological data parameter is an immune system marker selected from the group consisting of: C-reactive protein (CRP), IL-6, Serum Amyloid A (SAA), Haptoglobin, Pro-Calcitonin and Erythrocyte Sedimentation Rate (ESR).

12. The method of claim 1 wherein the periodicity of the subject's immune cycle is 7 days to 14 days.

13. The method of claim 1 wherein the three or more measurements of the physiological data parameter are taken at the same time of day.

14. The method of claim 1 wherein the three or more measurements are taken over a period of 3 to 15 days and are taken every day, every other day or three times a week.

15. The method of claim 1 wherein the future point in time when the subject will be in a pro-inflammatory phase is expressed as an entire day in which the subject will be in the pro-inflammatory phase and the preventative vaccination is administered at any time on that day.

\* \* \* \* \*